United States Patent [19]

Braithwaite

[11] Patent Number: 5,620,426
[45] Date of Patent: Apr. 15, 1997

[54] CONNECTING DEVICE

[75] Inventor: Philip W. Braithwaite, Worcester, United Kingdom

[73] Assignee: Innovata Biomed Limited, St. Albans, United Kingdom

[21] Appl. No.: 302,846

[22] PCT Filed: Apr. 7, 1993

[86] PCT No.: PCT/GB93/00734

§ 371 Date: Dec. 21, 1994

§ 102(e) Date: Dec. 21, 1994

[87] PCT Pub. No.: WO93/19808

PCT Pub. Date: Oct. 14, 1993

[30] Foreign Application Priority Data

Apr. 7, 1992 [GB] United Kingdom ............... 9207532

[51] Int. Cl.[6] ................................................. A61M 25/00
[52] U.S. Cl. ........................ 604/283; 604/323; 604/280; 137/625.48; 137/625.5
[58] Field of Search ....................... 137/625.4, 625.48, 137/625.5; 604/33, 245, 246, 247, 249, 283, 280; 128/762

[56] References Cited

U.S. PATENT DOCUMENTS

| | | |
|---|---|---|
| 3,964,331 | 6/1976 | Oldfield . |
| 4,291,706 | 9/1981 | Voges et al. . |
| 4,877,057 | 10/1989 | Christensen . |
| 5,100,377 | 3/1992 | Freitas et al. . |
| 5,247,966 | 9/1993 | Stevens et al. . |

Primary Examiner—Vincent Millin
Assistant Examiner—Perry E. Van Over
Attorney, Agent, or Firm—Edwin D. Schindler

[57] ABSTRACT

A connecting device for connecting together two or more medical instruments so as to allow, or control, the flow of fluid between the various medical instruments. The connecting device includes an intermediate conduit element having two inlets, to which the medical instruments may be connected, along with fluid directing members located inside the intermediate conduit element and able to move linearly therein. The fluid directing members are able to restrict, or allow, the flow of fluid, by way of the intermediate conduit element, between two or more medical instruments when they are connected to the conduit element, depending on the linear position of the fluid directing member inside the intermediate conduit element.

15 Claims, 18 Drawing Sheets

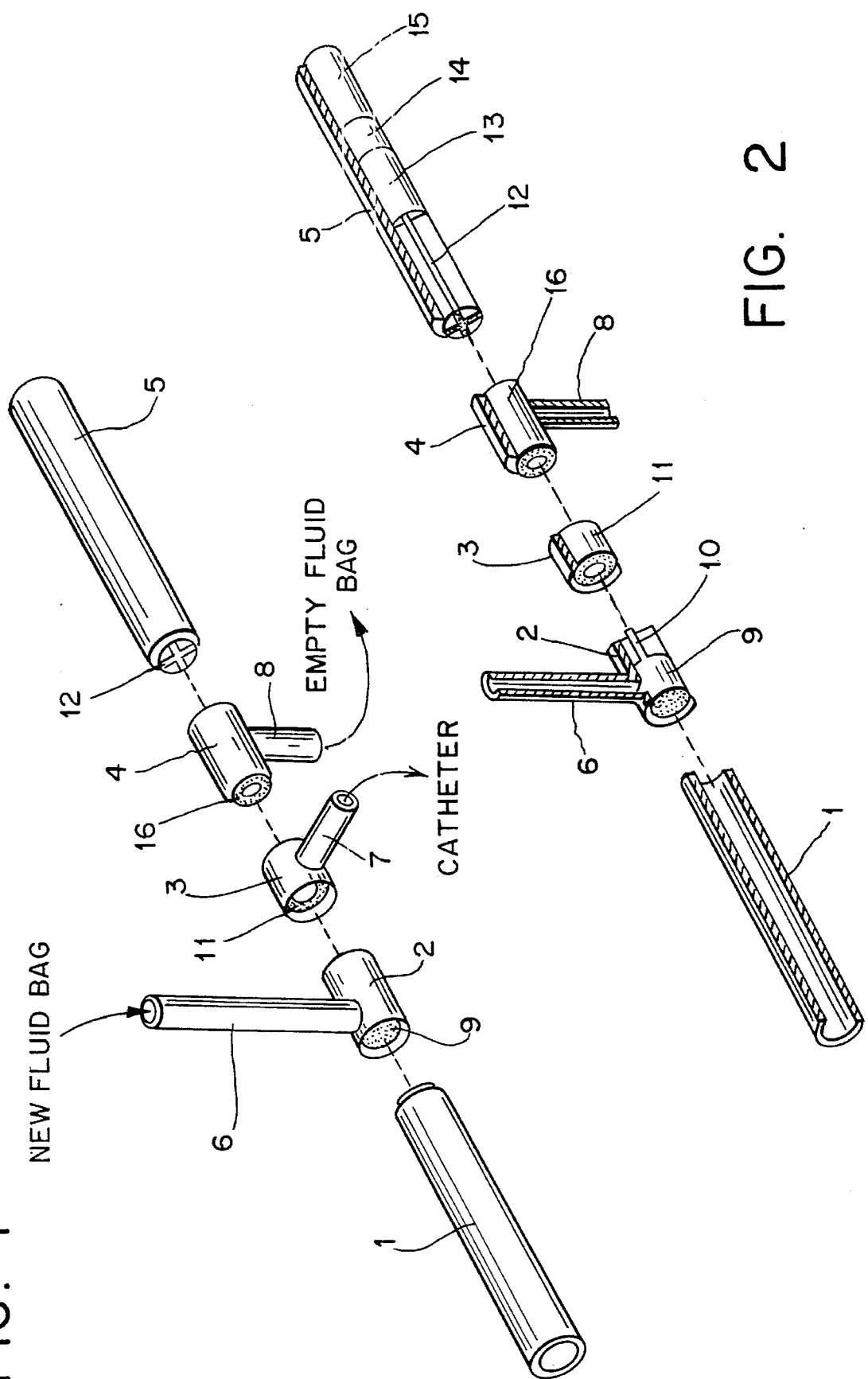

CONNECTING DEVICE

FIELD OF THE INVENTION

This invention relates to a device for connecting together two or more medical appliances, in particular although not necessarily appliances for use in dialysis, so as to allow and control the flow of fluid between the appliances. The invention also relates to parts for use in such a device, and to a method of connecting together two or more medical appliances using the device.

BACKGROUND TO THE INVENTION

There are a number of cases where the flow of fluids between two or more medical appliances has to be controlled. This fluid flow generally has to take place in a sterile environment so as to avoid the risk of infection, especially where the transfer of fluids into and out of a living body is involved. Difficulties are often encountered in connecting such appliances together to allow fluid transfer between them in a safe and hygienic manner.

Examples of situations in which medical appliances need to be connected together in this way include the administration of blood transfusions, intravenous delivery of drugs and nutrients, administration of anaesthetics and, more particularly, techniques involving dialysis. The latter usually involves infusion of fluids into, and draining of waste fluids from, the human body; in recent years, a large number of medical treatments have been developed which rely on such techniques. The usual method of infusing and draining the fluid is via a catheter implanted in the patient's body.

One example of such a treatment is "continuous ambulatory peritoneal dialysis" (CAPD), typically used on patients having kidney disorders. According to this treatment method, a relatively large amount of a specially formulated fluid is infused into the patient's peritoneum, from a sterile fluid bag, via a catheter implanted in the patient's abdomen. This fluid is retained in the peritoneum for a number of hours, usually between 6 and 12, and then drained from the body into an empty bag, again via the catheter, and immediately replaced by fresh fluid.

CAPD is a very effective form of treatment, allowing the patient to carry on a nearly normal life. However, patients undergoing CAPD are very susceptible to infection, which can give rise to peritonitis and frequently require hospitalisation. It is believed that the main source of infection to these patients is from airborne bacteria entering the catheter during the above described fluid bag exchange procedure.

In order to reduce the incidence of infection during the exchange of fluids in such treatment methods, various designs of connection system have been developed for connecting together the appliances involved (ie, in the case of CAPD, the catheter, the new fluid bag and the empty fluid bag). One known connection system comprises a bag of fresh fluid, coupled by means of a Y-piece connection to an empty fluid bag. Using this connector, the patient is required to open the catheter at least once on connection to the Y-coupler and once on disconnection, thus exposing the catheter to airborne bacteria. An alternative, more sophisticated, connection system comprises a coupling device which joins a new fluid bag and an empty bag and which opens a catheter automatically on connection thereto and closes it on disconnection. Such a device is relatively expensive to produce and not always simple to use.

None of the presently available connection systems is totally satisfactory in overcoming the problem of infection, and most suffer from other drawbacks such as lack of ease of use, comfort of wearing and/or reliability. There is therefore still a need for a connection system to control the flow of fluids between medical appliances, which system is not only safe to use (ie, avoiding the risk of infection and leakage) but also simple and convenient, so as to avoid the risk of incorrect usage by a patient or medical practitioner. It is therefore an aim of the present invention to provide a device for connecting together two or more medical appliances, which overcomes or at least mitigates the above described problems encountered in use of conventional connection devices.

STATEMENTS OF THE INVENTION

According to a first aspect of the present invention there is provided a device for connecting together the open ends of two medical appliances so as to allow and/or control the flow of fluid between the appliances, the device comprising an intermediate conduit means having two inlets to which the respective open ends of the two medical appliances may be connected; and a fluid directing means located inside the intermediate conduit means and moveable linearly therewithin, the fluid directing means being operable to allow or restrict the flow of fluid, via the intermediate conduit means, between the two appliances when said appliances are connected to the inlets of the conduit means, depending on the linear position of the fluid directing means inside the conduit means.

The primary advantage of the device of the present invention is that all fluid flow between the two medical appliances connected by means of the device can occur via the intermediate conduit means, which can be kept safely sterile for this purpose. Once the appliances have been connected to the inlets of the conduit means, control of the fluid flow into and out of the appliances is achieved by means of the fluid directing means, which moves entirely within the closed environment of the intermediate conduit means. The device is particularly useful in connecting together appliances such as catheters and fluid bags in medical techniques such as CAPD.

The device may be used to connect together a large number of different medical appliances, into and/or out of which fluid is to be allowed to flow. For instance, one of the appliances could comprise a supply of an anaesthetic gas, or of a drug or nutrient for intravenous supply, the other a tube or other conduit means for directing the flow of such fluids into a human or animal body. Thus, the term "medical appliances", as used in connection with the present invention, includes a simple tube which is to be used to supply fluids to the body or to some other apparatus or instrument. Also included in the term "medical appliance" are a catheter, and a bag into which or from which fluid is to be allowed to flow, for instance for use in CAPD or a similar technique.

The device may also be used to connect together more than two appliances. For instance, it is ideal for use during fluid exchange in CAPD, in which case, it may be used to connect together a catheter, a bag containing fresh fluid and an empty bag for drainage, so as to allow the control of fluid flow between the three appliances. Where the device is to be used to connect together a certain number of appliances, the intermediate conduit means of the device will comprise a corresponding number of inlets. The construction of the fluid directing means must then De such that its movement within the conduit means, in the region(s) of the inlets, is such as to allow or restrict the flow of fluid between the various appliances, depending on the position of the fluid directing means inside The conduit means.

Each of the medical appliances to be connected together using the device preferably at least includes an outlet tube or other conduit means (typically a flexible tube), the open end of which may be connected to one of the inlets provided in the intermediate conduit means of the device. The device may additionally comprise connecting means for connecting one of the appliances (conveniently via its outlet tube) either directly or indirectly to the appropriate inlet of the conduit means so as to allow for fluid flow between that appliance and the conduit means, when the fluid directing means occupies an appropriate position inside the conduit means. The connecting means may alternatively be provided on, or otherwise associated with, the open end of the medical appliance itself, rather than being provided as part of the device of the invention.

The inlets of the intermediate conduit means are preferably spaced longitudinally from one another along the conduit means. The fluid directing means is preferably moveable through the conduit means in a longitudinal direction, such that its longitudinal position within the conduit means determines whether fluid flow is allowed or restricted between two appliances connected to the device.

The intermediate conduit means preferably comprises a cylindrical tube, which is conveniently closed at both ends so as to maintain a completely sealed environment in which fluid flow between the two appliances may take place. In any case, the fluid directing means is preferably moveable within the conduit means between at least two positions, in one of which it allows the flow of fluid between two appliances connected to the device, whilst preventing escape of that fluid into regions of the conduit means not occupied by the fluid directing means. At each of its ends, the fluid directing means is thus preferably in sealing engagement with the internal walls of the conduit means, to prevent the flow of fluid from appliances connected to the device into regions of the conduit means beyond the ends of the fluid directing means.

The fluid directing means may comprise a single element, appropriately shaped so that its position within the conduit means determines whether or not, and if so in what way, fluid is allowed to flow between appliances connected to the device. For instance, it may be shaped so that as it moves along the conduit means past the inlets to which the appliances are connected, it operates to open and close those inlets in a desired sequence.

Alternatively, the fluid directing means may comprise a plurality of fluid directing elements, the positions of which within the conduit means determine the fluid flow allowed. Preferably, the fluid directing elements are moveable in succession longitudinally along the conduit means, so as to achieve the same effect as a single fluid directing element moving along the conduit means. In such an arrangement, for instance, one of the fluid directing elements may act to block the flow of fluid through an inlet in the conduit means as it passes that inlet, whilst another element in the succession of fluid directing elements may be operable to allow fluid flow through an inlet, and possibly into an adjacent or other inlet, as that element passes the inlet. Thus, the fluid directing elements may be of different shapes to one another.

Again, where the fluid directing means comprises a succession of fluid directing elements, those elements at the two ends of the fluid directing means are preferably in sealing engagement with the internal walls of the conduit means, so as to prevent the flow of fluid into regions of the conduit means not occupied by the fluid directing elements.

The fluid directing means is preferably moveable within the intermediate conduit means so as to be able to occupy at least one position in which all of the inlets of the conduit means are closed, thus preventing the flow of fluid between the conduit means and any medical appliances connected thereto. In order to achieve this, the outer edges of the fluid directing means must typically be in sealing engagement with the internal walls of the conduit means over at least part of the length of the fluid directing means, sufficient to obstruct the inlet(s) which are to be closed.

The fluid directing means is preferably operable to allow, as it moves longitudinally along the conduit means in one direction, a desired sequence of connections between medical appliances connected to the device. This allows the user to control a sequence of connections simply by moving the fluid directing means in one direction. For instance, the fluid directing means may be moveable from a first position, in which it acts to close all inlets in the conduit means to fluid flow; to a second position in which it allows the flow of fluid between two appliances connected to the device; to a third position in which all inlets are again closed to fluid flow between the conduit means and the appliances, this movement being a sequential movement, in one direction, from each position to the next.

Where the fluid directing means comprises a number of separate fluid directing elements, those elements are preferably positioned inside the conduit means in end-to-end abutting relationship. Typically, they will include one or more sealing elements, of appropriate length, the outer walls of which are in use in sealing engagement with the internal walls of the conduit means, so as to close one or more of the inlets to fluid flow. Each sealing element may take the form of a plug, preferably of a resilient material, which whilst sitting inside the conduit means in sealing engagement with its internal walls, is nevertheless capable of sliding movement along the inside of the conduit means.

The fluid directing elements will typically also include one or more elements which are so shaped as to allow fluid flow between two inlets when the elements are appropriately positioned in the conduit means.

Those fluid directing elements which allow fluid flow between inlets of the conduit means may simply take the form of spacers which maintain an appropriate spacing between sealing elements of the fluid directing means, the spacers being so shaped as to allow fluid flow around them between two or more inlets (depending on the length of the spacer concerned). Alternatively, such an element might be in the form of a plug, the outer walls of which are in sealing engagement with the internal walls of the conduit means, the plug having an internal duct, open at appropriate positions to allow the flow of fluid between two or more inlets in the conduit means when the plug is appropriately positioned. Such a plug is again preferably made from a resilient material.

Other fluid directing elements may, for instance, be of such a shape as to allow fluid flow between two inlets, whilst simultaneously obstructing a third inlet positioned in the conduit means between the first two. The exact shapes of the fluid directing elements will naturally depend on the exact form of fluid connection which they are to allow between the various appliances connected to the device. Thus, as the fluid directing elements move in sequence along the conduit means, they will act to allow a desired sequence of connections between the connected appliances.

In a preferred embodiment of the invention, the intermediate conduit means is in part made up of the connecting means for one or more medical appliances to be connected using the device, such that appropriate positioning of the connecting means relative to other parts of the conduit means results in the formation of a complete conduit means through which fluid flow, and movement of fluid directing elements, may be allowed.

For instance, the connecting means of one or more of the appliances may comprise an open ended hollow tube of an appropriate length, having in its side wall an inlet to which the appliance may be connected. This tube section may be positioned in use to form part of a longer length of tube which constitutes the intermediate conduit means of the device of the invention.

Each appliance connecting means which, in use of the device, forms a separable part of the intermediate conduit means, preferably comprises a sealing means which seals the open end(s) of the connecting means against escape of fluid from the appliance when not connected to the conduit means. The sealing means preferably constitutes, in use, a fluid directing element in the device. Thus, the sealing means might take the form of a resilient plug, located inside the connecting means so as to sit in sealing engagement with its internal walls. When, in use, the connecting means forms part of an overall conduit means, this plug will then be moveable through the conduit means in a longitudinal direction, along with other fluid directing elements, and may thus be displaced from the connecting means so as to allow the flow of fluid to and from the relevant appliance when necessary.

In such a case, the fluid directing means of the device preferably comprises at least one further, separate, sealing means for each appliance to be connected to the conduit means via a separable connecting means. After use of the device, these further sealing means may be moved along the conduit means so as to locate inside respective separable connecting means, allowing those connecting means to be removed from the device because they are thereby sealed against fluid loss from the appliance with which they are associated.

This preferred form of the device of the invention is particularly advantageous because it allows for a closed environment to be maintained at all times during connection of medical appliances to the device, flow of fluid between them via the intermediate conduit means and removal of the appliances. A sterile environment is thus maintained at all times.

Each appliance, before connection to the device, is sealed at its closed end by means of a separate sealing means located in the connecting means of the appliance. The sealing means is then displaced from the connecting means as it, and other fluid directing elements, are moved along the conduit means by the user to effect the desired sequence of fluid connections. Finally, when all fluid flow is completed, the connecting means of each appliance is again sealed by means of a separate sealing means forming part of the overall fluid directing means of the device. Each appliance, and its associated connecting means, may therefore be separated from the device, completely sealed at its open end and without the need for fluid in the appliance to come into contact with the outside environment at any time during use of the connecting device.

Such a device is also relatively simple and inexpensive to manufacture. It is simple to use, requiring very little manual dexterity or intelligence for its effective operation. It is thus ideal for use in techniques such as CAPD where patients may need to effect fluid exchange themselves. Because of the simplicity of the device, and its constituent components, it can be relatively small, lightweight and compact, thus being easily portable.

Moreover, the separate connecting means of the medical appliances, which in use will form part of the intermediate conduit means of the device, will typically be supplied with the medical appliances themselves. For instance, a patient using the device in CAPD will simply obtain a new fluid bag having a connecting means attached to its outlet tube, a sealing means being ready in place inside the connecting means and the whole appliance thus being immediately ready for connection to the device of the invention. Similarly, a catheter would typically be supplied with an appropriately shaped connecting means already attached to it, and sealing means inside the connecting means.

A device in accordance with the invention preferably additionally comprises drive means for moving, or for assisting the movement of, the fluid directing means within the intermediate conduit means. This drive means may take the form, for instance, of a plunger, operable from outside one end of the conduit means, which may be depressed so as to push the fluid directing means through the conduit means. The drive means may alternatively be automatic in operation, for instance under mechanical, electrical or hydraulic control. It may provide a stepped or a continuous movement of the fluid directing means, and may for instance be automatically controlled so as to effect a pattern of movement of the fluid directing means which results in a desired sequence of fluid flow connections between appliances connected to the device, due to the sequence of positions thereby occupied by the fluid directing means within the conduit means.

The device preferably additionally comprises support means for the intermediate conduit means. Preferably, the support means is also suitable for mounting the connecting means of medical appliances thereon, in the correct sequence, when the appliances are connected to the conduit means. The support means of the device may, for instance, comprise a base, having clips thereon for clipping into position on the base the connecting means of the medical appliances and/or outlet tubes attached to the appliances. It may comprise an appropriately shaped housing to receive and protect the intermediate conduit means and any additional connecting means during use.

Any drive means of the device is conveniently located in or on the support means. In a preferred embodiment of the invention, the drive means is operable to drive a series of fluid directing elements through the intermediate conduit means, from one location in or on the support means to another location. It may be operable to create movement of the elements in more than one direction, and may additionally comprise control means (which may be automatic or user operated) for controlling the movement as desired. The drive means may comprise a chain of pushing elements which act to push the fluid directing means in a desired direction and are driven, in conventional fashion, through the conduit means. In use, the pushing elements and the fluid directing means preferably form a closed loop which can be driven backwards or forwards through the conduit means so that the device need not be reset after each use.

In the particular case where the device of the invention is for use in CAPD, for controlling fluid flow between a catheter, a receiver bag for receiving fluid drained from a body via the catheter and a fresh fluid bag containing fresh fluid to be infused into the body via the catheter, the device preferably comprises a first fluid directing element which allows, when positioned in use adjacent the fresh fluid bag inlet and the receiver bag inlet, the flow of fluid from the fresh fluid bag to the receiver bag but not into or out of the catheter; a second fluid directing element which allows, when positioned in use adjacent the catheter inlet and the receiver bag inlet, the flow of fluid from the catheter to the receiver bag but not into or out of the fresh fluid bag; a third fluid directing element which allows, when positioned in use adjacent the fresh fluid bag inlet and the catheter inlet, the flow of fluid from the fresh fluid bag to the catheter but not into or out of the receiver bag; and a fourth fluid directing element or series of elements, which when positioned in the conduit means across the catheter inlet and the two bag inlets, acts to prevent the flow of fluid between the conduit means and any of the appliances.

In such a device, the fluid directing elements may alternatively take the form of a single fluid directing means, of such a shape that it is capable of achieving the same function as the four separate fluid directing elements, as its longitudinal position varies in the conduit means. The four fluid directing elements, or the equivalent parts of the fluid directing means, are preferably arranged to pass through the conduit means one after the other, in the order specified above, so as to effect a correct sequence of fluid connections between the catheter, the receiver bag and the fresh fluid bag.

The device of the invention may additionally comprise one or more valves, for or use in further controlling the flow of fluid to or from the medical appliances connected to the intermediate conduit means.

According to a second aspect of the present invention there is provided a connecting means for use as part of the device of the first aspect of the invention, the connecting means being capable of attachment to the open end of a medical appliance and forming, in use in the device, part of the intermediate conduit means of the device, such that fluid may be allowed to flow between the open end of the medical appliance and a second medical appliance also connected to the device, via the intermediate conduit means.

This connecting means is preferably in the form of a length of hollow tube, and preferably contains a sealing means for sealing the open end of a connected medical appliance, which sealing means forms part of the fluid directing means in use of the overall device.

The present invention also provides, according to a third aspect, a medical appliance, to the open end of which such a connecting means is attached.

According to a fourth aspect of the present invention, there, is provided a fluid directing means for use as part of the device of the first aspect, which fluid directing means is capable of being positioned inside, and of (preferably longitudinal) movement within, the intermediate conduit means of the device. The fluid directing means may comprise a single fluid directing element of an appropriate shape, or a number of separate fluid directing elements which may be moved through the conduit means in succession. The fluid directing means must, in use, be capable of being used to control the flow of fluid between medical appliances connected to the device, according to its position within the conduit means.

According to a fifth aspect of the present invention, there is provided a method for controlling the flow of fluid between two or more medical appliances, the method comprising the connection of the appliances to, and use of, a connecting device according to the first aspect of the invention.

According to a sixth aspect of the invention, there is provided support means for use as part of a device in accordance with the first aspect. The support means preferably includes drive means for moving, or for assisting the movement of, the fluid directing means within the intermediate conduit means. Conveniently, the support means is in the form of, or comprises, a housing for receiving and protecting the intermediate conduit means during use of the device.

Also within the scope of the invention is a device as described above for use in connecting together two medical appliances, where one of the appliances is for use in adding fluid to, or removing fluid from, the other. For instance, one of the appliances may be a syringe for use in injecting a medication into a catheter or other appliance connected to a patient's body. The fluid directing means is again used to allow or restrict the flow of fluid between the two appliances, according to its position-within the conduit means. The fluid directing means may, if necessary, be biassed by biassing means into a position in which it obstructs the flow of fluid into or out of one of the appliances, but be moveable out of this position, against the action of the biassing means, in order to permit the desired fluid flow. Again, one or more of the appliances preferably has connecting means which itself forms part of the intermediate conduit means in use of the device.

The present invention will now be described, by way of example only, with reference to the accompanying illustrative drawings, of which:-

FIGS. 1 and 2 show exploded perspective views of a connecting device in accordance with the present invention;

DETAILED DESCRIPTION OF THE DRAWINGS

Figure 3A:
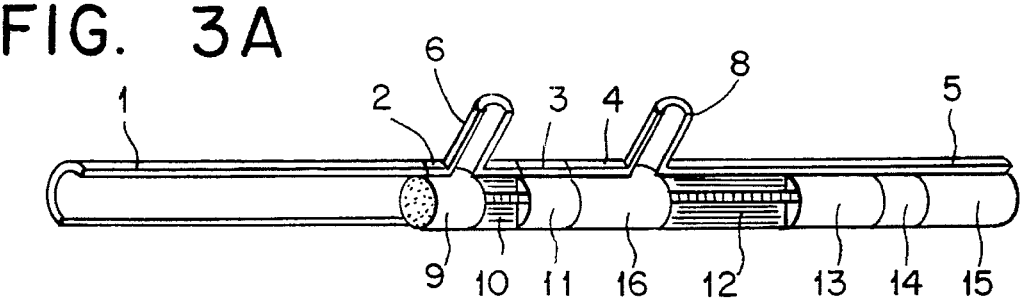
FIG. 3 shows the device of FIGS. 1 and 2 in use.

Referring firstly to FIGS. 1 and 2, there is shown in exploded perspective view a connecting device in accordance with the invention, used to connect together a catheter and fluid bags during a fluid exchange procedure (for instance, for use in CAPD).

The device comprises an intermediate conduit means which, in use, is made up of components 1–5, positioned adjacent one another to achieve communication along the entire length of the assembled conduit means. Each of the components 1–5 comprises a length of hollow tubing. The ends of these lengths of tubing are shaded (tapered) so as to cooperate with and engage adjacent ends of connecting components when assembled.

Connecting component 2 also functions as a connecting means for a fluid bag (not shown) containing fresh dialysis fluid, the open end of which is connected to tube 6 set in the side wall of component 2. In a similar manner, component 3 is a connecting means for a catheter, via tube 7, and component 4 a connecting means for an empty fluid bag (into which dialysis fluid is to be drained from the catheter), via tube 8.

Prior to use of the device, when the catheter and the two fluid bags are brought together as shown for assembly, the component 2 contains a resilient plug 9, which acts to seal closed the open end of the new fluid bag. From FIG. 2, which is a part sectional view of the components shown in FIG. 1, it can be seen that the plug 9 carries a spacer 10.

Connecting component 3 contains a hollow resilient seal 11, through the centre of which fluid may flow in a longitudinal direction. This seal prevents the flow of fluid into or out of a catheter connected to component 3, since the outer walls of the seal 11 sit in sealing engagement with the internal walls of tube 3, as do the outer walls of plug 9 in tube 2.

Finally, component 4 contains a further hollow resilient seal 16, which again permits the flow of fluid through tube 4 in a longitudinal direction, but not into or out of side tube 8 which leads to the empty fluid bag.

Component 5 contains, prior to use of the device, a spacer 12, a hollow resilient seal 13, a further hollow resilient seal 14 and a resilient plug 15, the outer walls of the seals and plugs being in sealing engagement with the internal walls of component 5. Component 1 is empty prior to use of the device.

A typical method of use of the device shown in FIGS. 1 and 2 is described with reference to FIGS. 3A–E, all of which show the device in perspective view with part of the intermediate conduit means cut away for clarity.

Firstly, components 1–5 are assembled together as shown in FIG. 3A, to form a complete intermediate conduit means. The components are actually held in a support means not shown in FIG. 3 (see FIGS. 4 and 5), to ensure that all components remain in their correct positions during use.

Figure 3B:
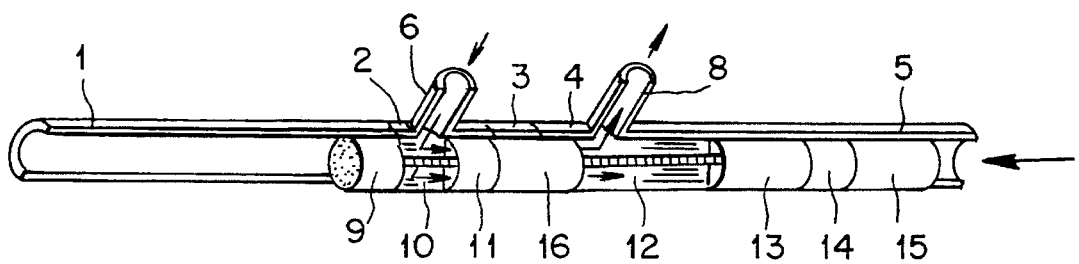

When a user is ready to commence fluid exchange between the old and new fluid bags and the catheter, he pushes the entire series of seals, plugs, and spacers ("fluid directing elements" 15, 14, 13, 12, 16, 11, 10 and 9) in a longitudinal direction along the conduit means, as shown by the long arrow in FIG. 3B. This results in the fluid directing elements occupying the positions shown in FIG. 3B. Fresh fluid from the new fluid bag connected at 6 can now enter the tube 2, flow around spacer 10, flow through the hollow seals 11 and 16 and around spacer 12 and enter the empty fluid bag connected at 8. The user allows a small amount of fluid to pass between the two fluid bags in this way, so as to effect flushing of the assembly using fresh, sterile fluid from the new fluid bag. The short arrows in FIG. 3B indicate the direction of flow of fluid during this stage of operation of the device.

Figure 3C:
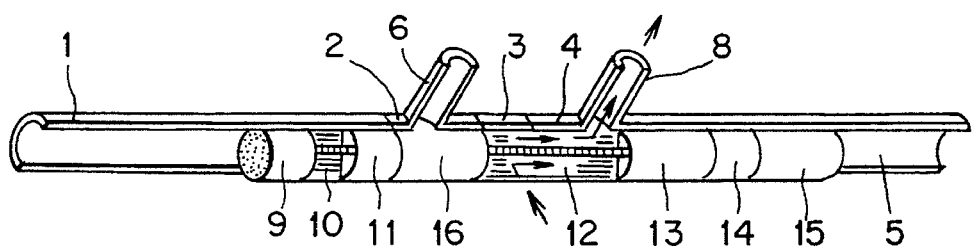

In the next stage, the user pushes the fluid directing elements yet further in the direction shown by the long arrow in FIG. 3B, resulting in the situation shown in FIG. 3C. Here, the new fluid bag is sealed from the conduit means by seal 16. However, fluid is now permitted to flow from the catheter, around spacer 12, and out into the empty fluid bag through tube 8. In this way, fluid from the patient's body may be drained, via the catheter, into the empty fluid bag.

Figure 3D:
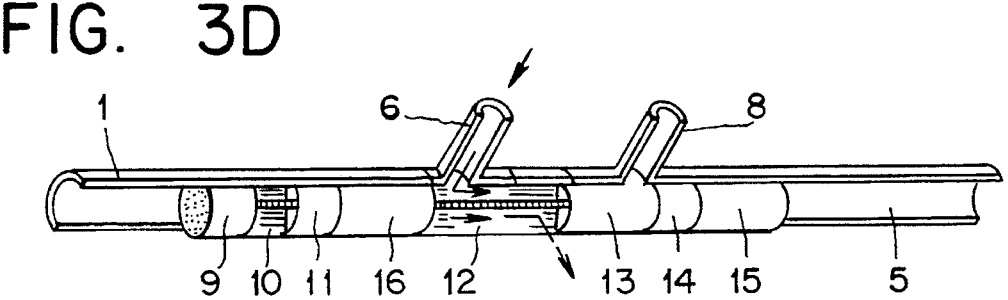

When this part of the operation has been completed, and the patient is ready to infuse fluid from the new fluid bag, he once again pushes the fluid directing elements through the conduit means, to reach the position shown in FIG. 3D. Fluid from the new bag is now able to flow around spacer 12, down tube 7 (not seen in FIG. 2) and into the patient's body via the catheter. The fluid bag containing the drained fluid is sealed from the conduit means by seal 13.

Figure 3E:
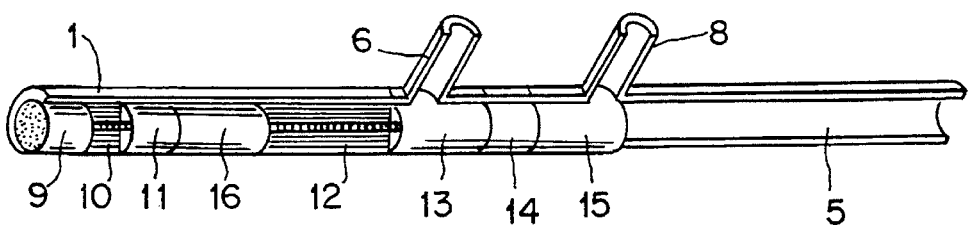

Finally, once infusion is completed, the fluid directing elements are pushed to the position shown in FIG. 3E. Both fluid bags, and the catheter, are now sealed from the conduit means by seals 13, 14 and 15. The catheter can be removed from the device, together with its connecting component 3 which is sealed by seal 14. The whole exchange of fluids has taken place in a completely closed environment within the conduit means, without the need to expose the open ends of any of the appliances to the outside air.

After use, the device is disassembled. Component 1, containing the used fluid directing elements 9, 10, 11, 16 and 12, is discarded. The now empty tube 5 is set aside for use in a subsequent fluid exchange, in which it will be used in the same way as component 1 was used in the exchange process described above. The bag containing the drained fluid is disposed of, together with connecting component 4. The now empty "new" fluid bag, with its connecting component 2, is set aside, again for use in a subsequent exchange process, in which it will be filled with drained fluid. The catheter connecting component 3, with its sterile sealing plug 14, is placed inside a protective cover (not shown) and attached to the patient in a secure and comfortable position.

When the device is to be used subsequently, a fresh tube such as 5 in FIGS. 1 and 2, pre-loaded with the correct arrangement of fluid directing elements, needs to be connected to the catheter connecting means 3, the component 2 with the empty fluid bag, a new fluid bag having a connecting component similar to 2 and the now empty component 5.

Thus, it will be seen that the device shown in FIGS. 1–3 is relatively simple to use and re-use, and has the advantage of maintaining a sterile environment at all times whilst fluid is being exchanged.

Figure 4:
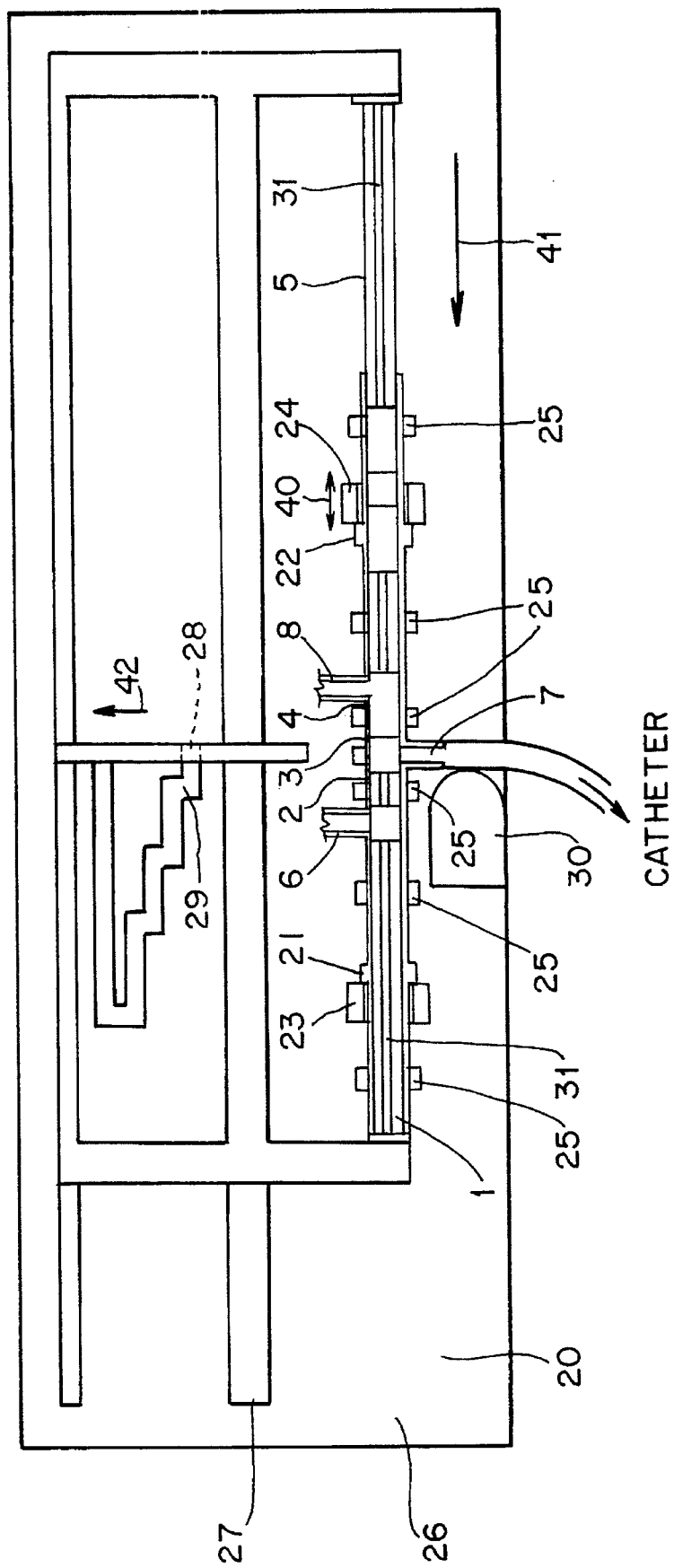
FIG. 4 is a plan view of the device of FIGS. 1–3, in an appropriate support means.

FIG. 4 shows a schematic plan view of a holding device or support means which may be used to hold the various components of the device shown in FIGS. 1–3 in position during use. As can be seen from FIG. 4, the various components are mounted on a plastics supporting base 20. Components 1 and 5 have flanges 21 and 22 respectively incorporated on them, these flanges being positioned adjacent to blocks 23 and 24 respectively. Block 23 is fixed to the base 20, whereas block 24 is moveable in a longitudinal direction, as shown by the arrows 40.

The connecting components 2, 3 and 4 are mounted in brackets 25. The moveable block 24 is then moved in a direction towards block 23 and locked (locking device not shown) so as to effect sealing of the adjacent connecting faces of the various components (by engagement of the "male" and "female" tapering ends of those components, as seen in FIG. 1). A frame 26 is slidably mounted in groove 27 in the base 20, and a "key" 28 is in turn slidably mounted in frame 26. A shaft 31, on which the fluid directing elements are mounted, is attached at either end to the frame.

Figure 5A:
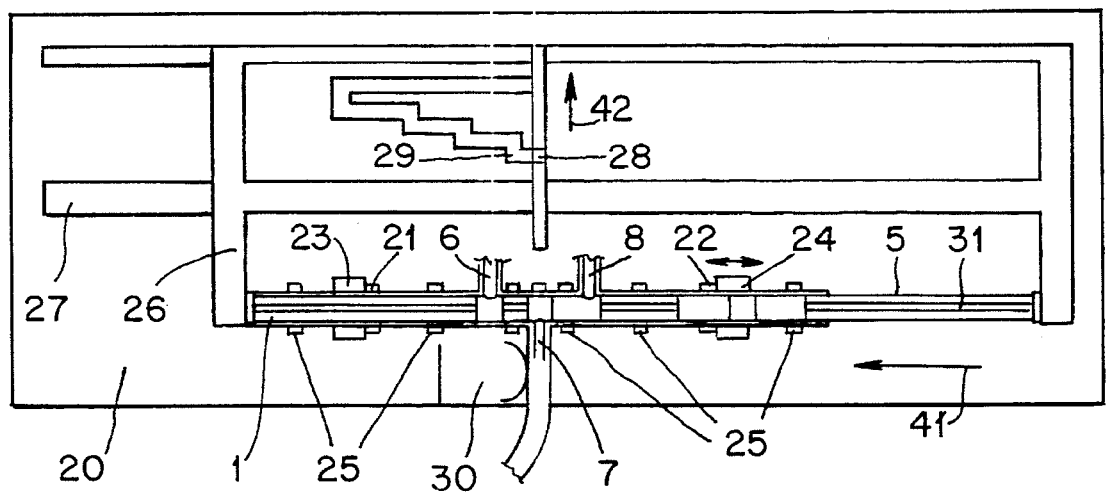
FIG. 5 shows the device and support means, as in FIG. 4, during use of the device.
Figure 5B:
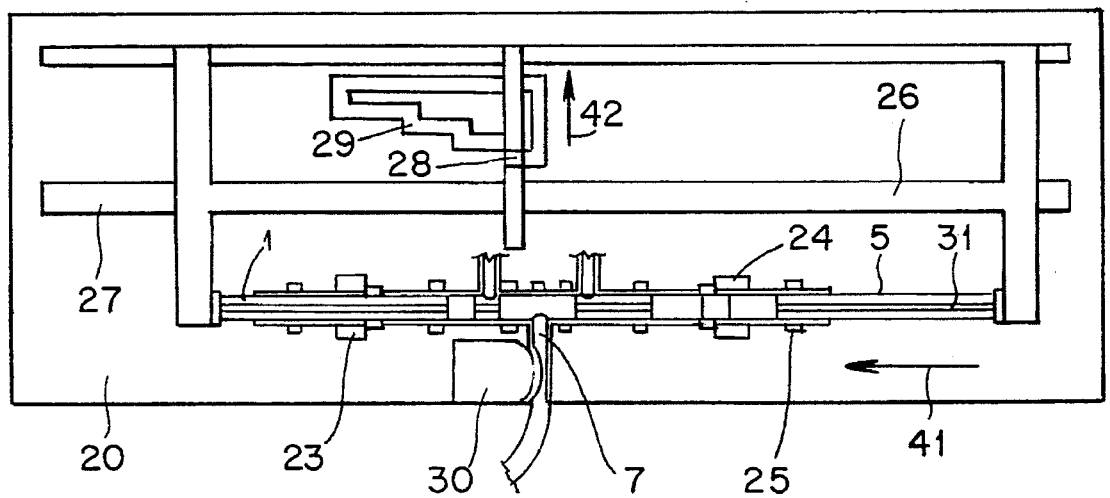
Figure 5C:
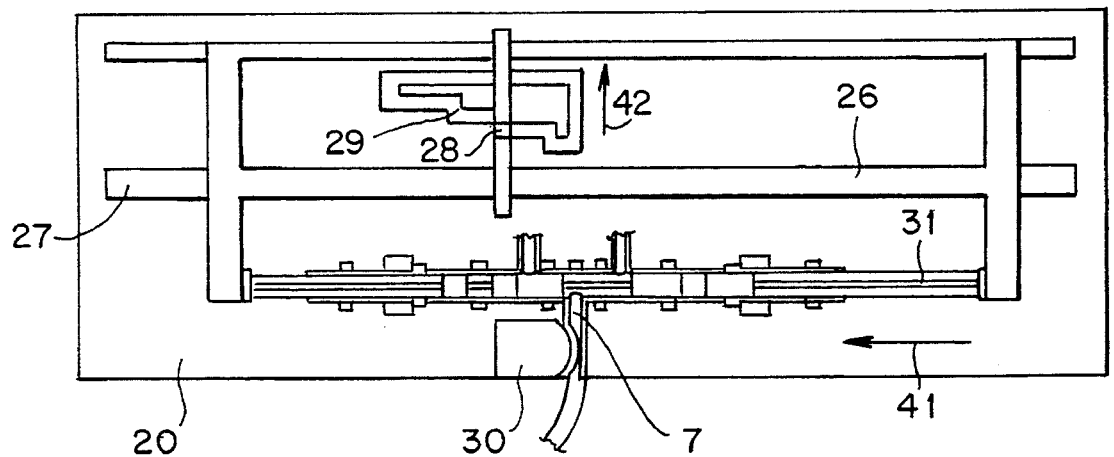

Operation of the device as shown in FIG. 4 is illustrated schematically in FIGS. 5A–5C. These figures show, in plan view, the relative positions of the various parts of the device and support means, during three successive stages of operation of the device.

It can be seen that pushing frame 26 in the direction shown by arrow 41 in FIGS. 4 and 5 causes the various fluid directing elements of the device to be pushed through the inside of the conduit means to effect the correct sequence of fluid connections between the old and new fluid bags and the catheter (appliances not shown in FIGS. 4 and 5). Pushing frame 26 firstly results in key 28 contacting the first step of the stepped keyway 29. The fluid directing elements then occupy their second position, ie that shown in FIGS. 3B and 5B. In order to move the fluid directing elements into their next position (FIG. 3C), the key 28 is pushed in the direction of arrow 42, until it contacts the second step of the keyway 29 (FIG. 5C). Continuing movement of key 28, along the keyway 29, allows the user to effect a stepped movement of the fluid directing elements through the conduit means, from one stage of operation of the device to the next, in the correct way.

Once fluid exchange has been completed, the moveable block 24 is released, the various components of the device lifted away from the supporting base 20 and the frame 26 returned to its starting position, as seen in FIG. 4.

In practice, the flow of fluid into and out of the patient's abdomen via the catheter has to be controlled. This control is achieved by the addition of a variable clamping means 30, mounted on the base 20, which may be used to reduce the flow into or out of the catheter connecting tube 7. The clamp 30 is simply moved in a direction towards the flexible catheter tube, so as to squeeze it and restrict the flow of fluid through it (see, e.g. FIGS. 5B and C). Movement of the clamp 30 may be achieved in a variety of ways, for instance via a cam or screw action.

Figure 6A:
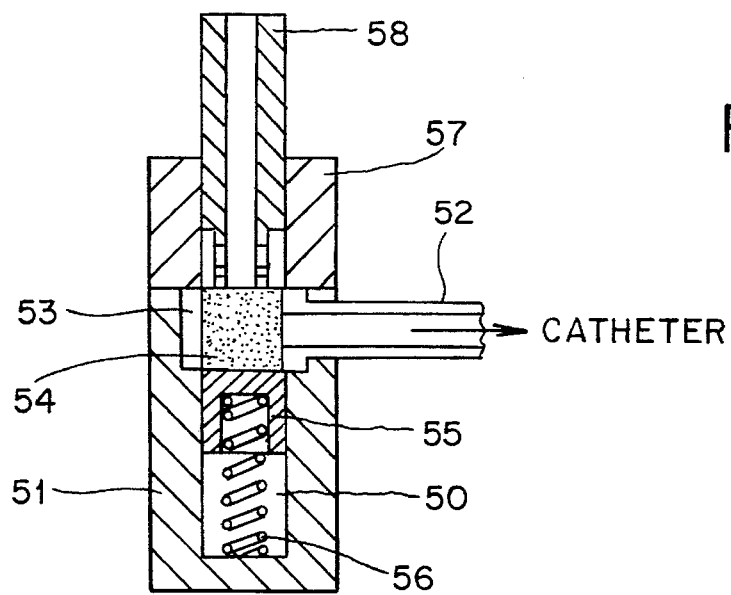
FIG. 6 shows an alternative device in accordance with the invention, used to add fluid to, or remove it from, a medical appliance.
Figure 6B:
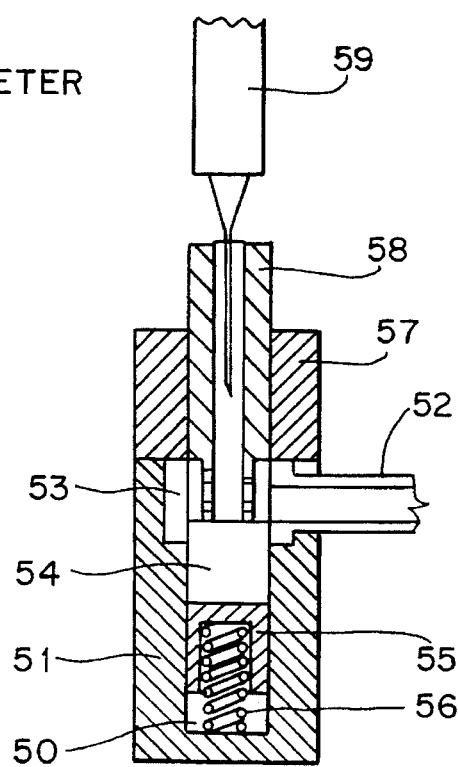

Referring now to FIG. 6, there is shown an alternative connecting device in accordance with the invention, which may be used to facilitate injection of a medication into, or removal of samples of fluid from, a catheter. The device is shown in schematic cross-section, FIGS. 6A and 6B corresponding to different stages during its use.

The device comprises an intermediate conduit means 50, in the form of a bore in receptacle 51. The open end of the catheter (tube 52) is connected to a connecting means 53, similar to component 3 in the device shown in FIGS. 1 and 2 (ie, it has the form of a length of hollow tube). A resilient sealing plug 54 is positioned inside tube 53, to seal the open end of the catheter. The connecting means 53, in use of the device, forms part of the intermediate conduit means 50.

Below the connecting means 53 there is positioned a spring retainer 55, which holds a biassing spring 56 in position inside the closed end of the conduit means 50. The spring is shown in FIG. 6A in its "at rest" position. However, downward movement of the plug 54 must take place against the action of spring 56, which therefore biasses the plug 54 into a position in which it seals the catheter shut.

In use of the device, the catheter connecting means 53 is positioned as shown in FIG. 6A, and clamped in place using the closing element 57. A plunger 58 is then pushed down through a central bore in closing element 57, pushing the plug (fluid directing element) 54 spring retainer 55 downwards, against the action of spring 56. The plunger may then be locked in this position by locking means (not shown in FIG. 6), and a second medical appliance such as a conventional syringe (59 in FIG. 6B) introduced through the open end of the plunger. Once the necessary fluids have been injected and/or removed using syringe 59, it is removed from the plunger, the plunger is unlocked from its position in the closing member 57 and spring 56 once again urges the plug 54 back into position inside the catheter connecting means 53. The catheter and its connecting means can then be safely removed from the device, its open end having remained sterile at all times during the injection and/or removal of fluid.

Referring now to FIGS. 7–11, an alternative connecting device in accordance with the invention is shown in perspective view (exploded in FIG. 7), with parts of the intermediate conduit means cut away for clarity. This device is again shown in use for effecting fluid exchange between a catheter, a fresh dialysis fluid bag and an empty fluid bag, during CAPD.

Figure 7:
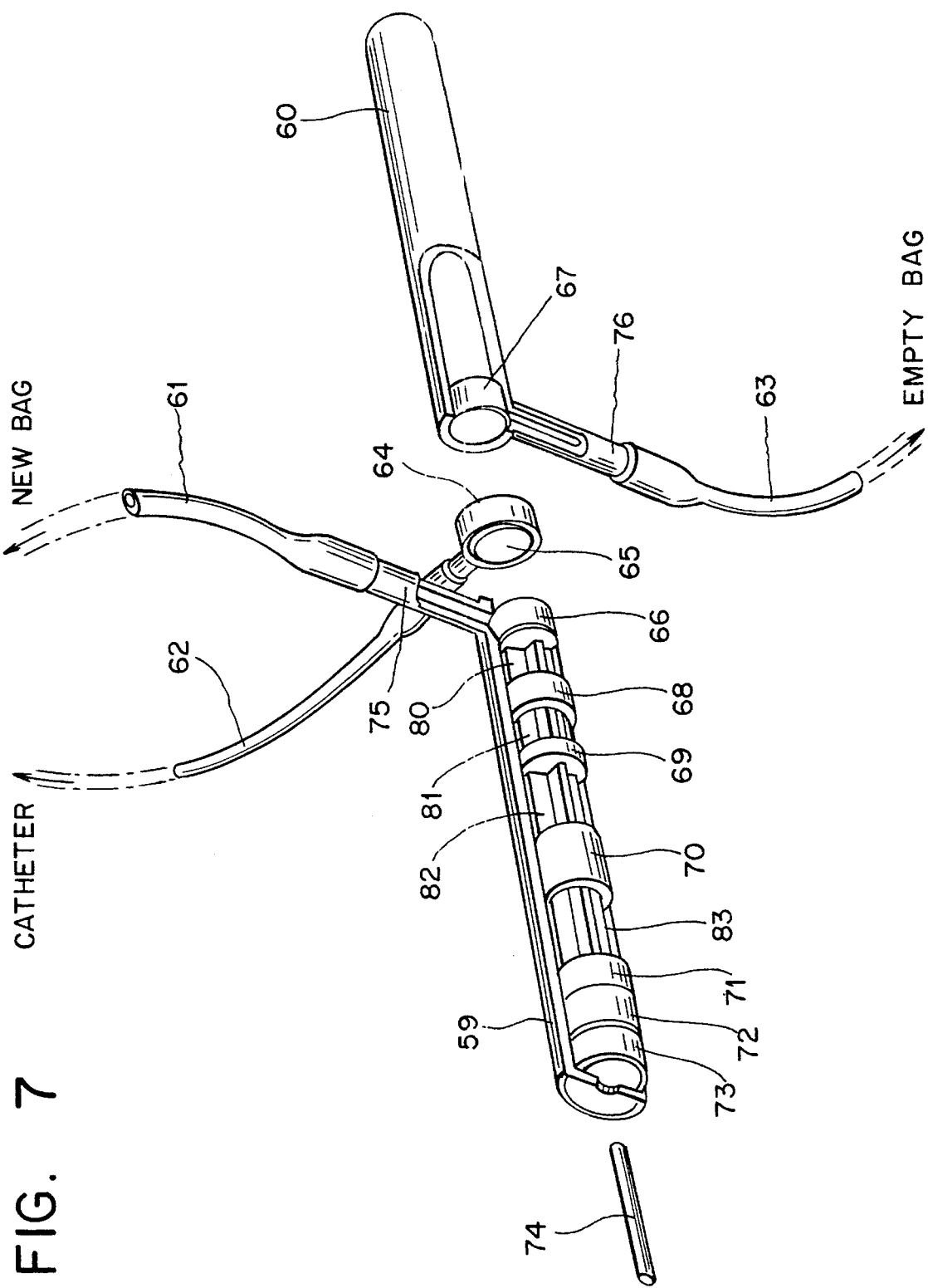
FIG. 7 is an exploded perspective view of a further connecting device in accordance with the invention.

In FIG. 7, the device is seen to comprise an intermediate conduit means made up, in use, from tube 59, tube 60 and the connecting means 64 for the catheter (a snort length of hollow tube). Tubes 59 and 60 are each closed at one end and open at another, the open end being for connection adjacent the connecting means 64 of the catheter.

Component 59 has an inlet via tube (connecting means) 75, to which the open end of a fresh fluid bag is connected via flexible tube 61. Component 60 has a similar connecting tube 76, to which the open end of an empty fluid bag is connected via flexible tube 63. The device is thus suitable for use with any conventional fluid bag; the bag does not need to be provided with special connecting means designed specifically for use in the device.

The fluid directing elements contained within the conduit means are the following: a plug 65, sealing the catheter connecting means 64; a plug 67, sealing the outlet to the empty bag; a plug 66 sealing the outlet to the fresh fluid bag; a spacer 80; a hollow seal 68; a spacer 81; a plug 69; a spacer 82; a plug 70; a spacer 83; and three further plugs 71–73 All of the fluid directing elements have their outer surfaces in sealing engagement with the internal walls of the tubes 59,60 and 64.

A manually operated plunger 74, at the left hand end of tube 59 as shown in FIG. 7, is used to push the fluid directing elements along the length of tubes 59, 64 and 60, in a direction from left to right as shown in FIG. 7. This movement has the following effects.

Figure 8:
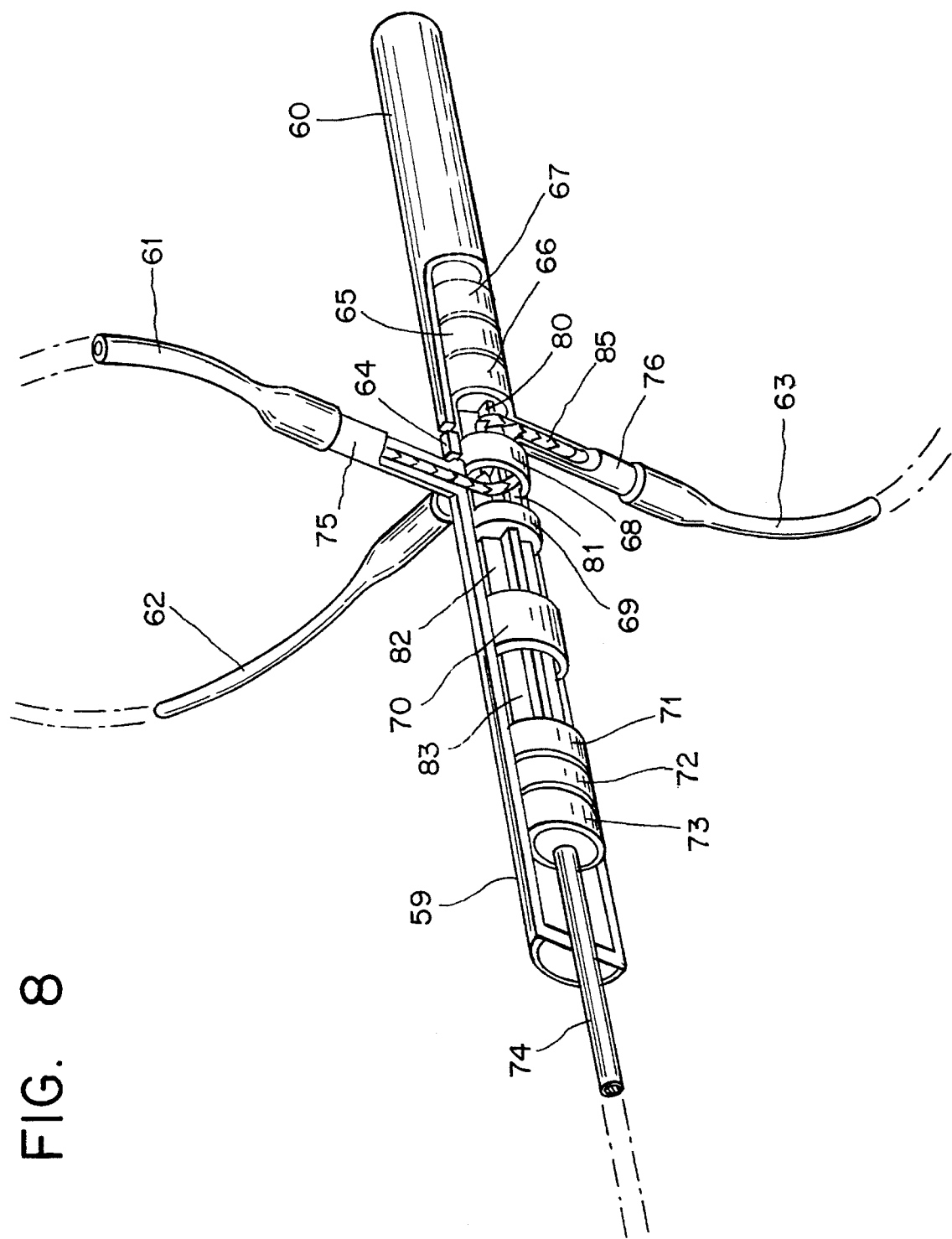
FIGS. 8–11 are perspective views of the device shown in FIG. 7, during various stages of its use.
Figure 9:
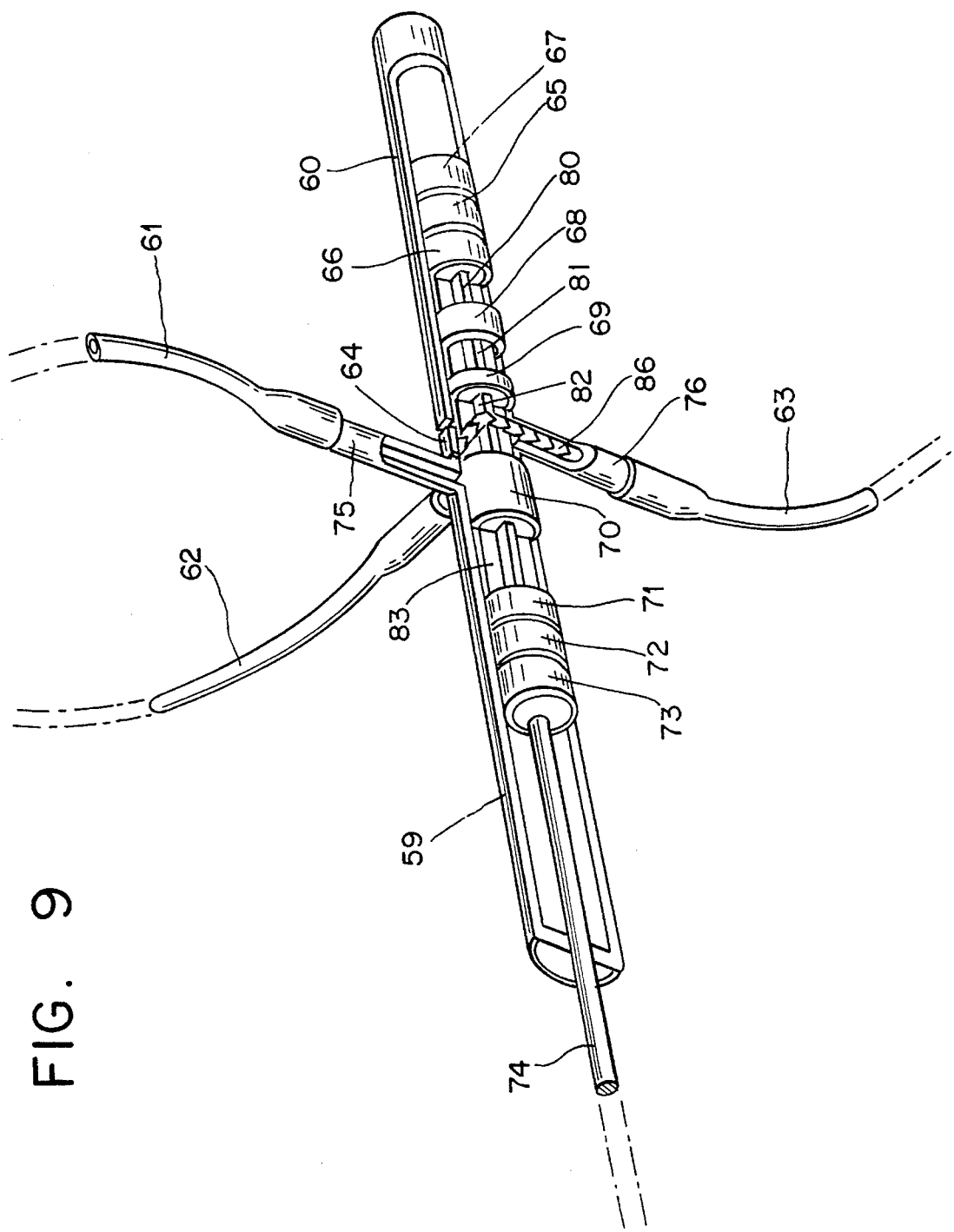

Firstly, the sealing plugs 65–67 are pushed along the conduit means until they reach the position shown in FIG. 8, and no longer obstruct the outlets to either the fluid bags or the catheter. At this stage, fluid 85 is allowed to flow from the fresh fluid bag, via tube 75, around the spacer 81, through the hollow seal 68, around spacer 80 and into the empty fluid bag via tubes 76 and 63. This is allowed to continue for sufficient time to flush the inside of the conduit means with fluid from the fresh fluid bag. The fluid directing elements are then pushed further along the conduit means, to the position shown in FIG. 9.

Fluid is now allowed to drain from the catheter into the empty fluid bag, via tube 62, around spacer 82 and through connecting tubes 76 and 63. This fluid flow is indicated at 86.

Figure 10:
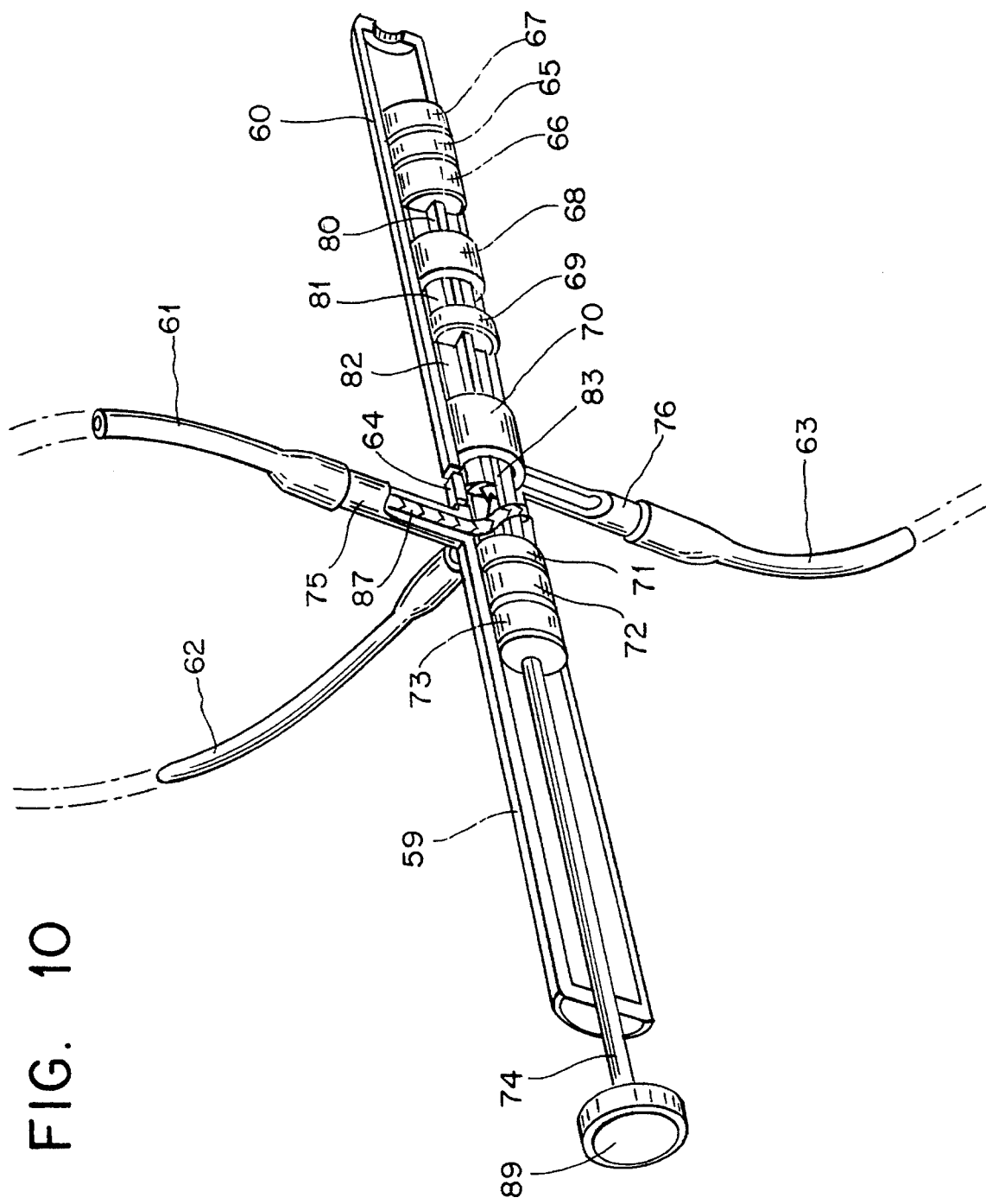

Further movement of the fluid directing elements results in the situation shown in FIG. 10, where fluid flow shown at 87 is allowed between the fresh fluid bag and the catheter, around spacer 83. In this position, the sealing plug 70 prevents the flow of fluid into or out of the empty bag via tube 76, just as it prevented flow to and from the fresh fluid bag in the position shown in FIG. 9.

In FIG. 10, the reference numeral 89 refers to the end of the plunger 74.

Figure 11:
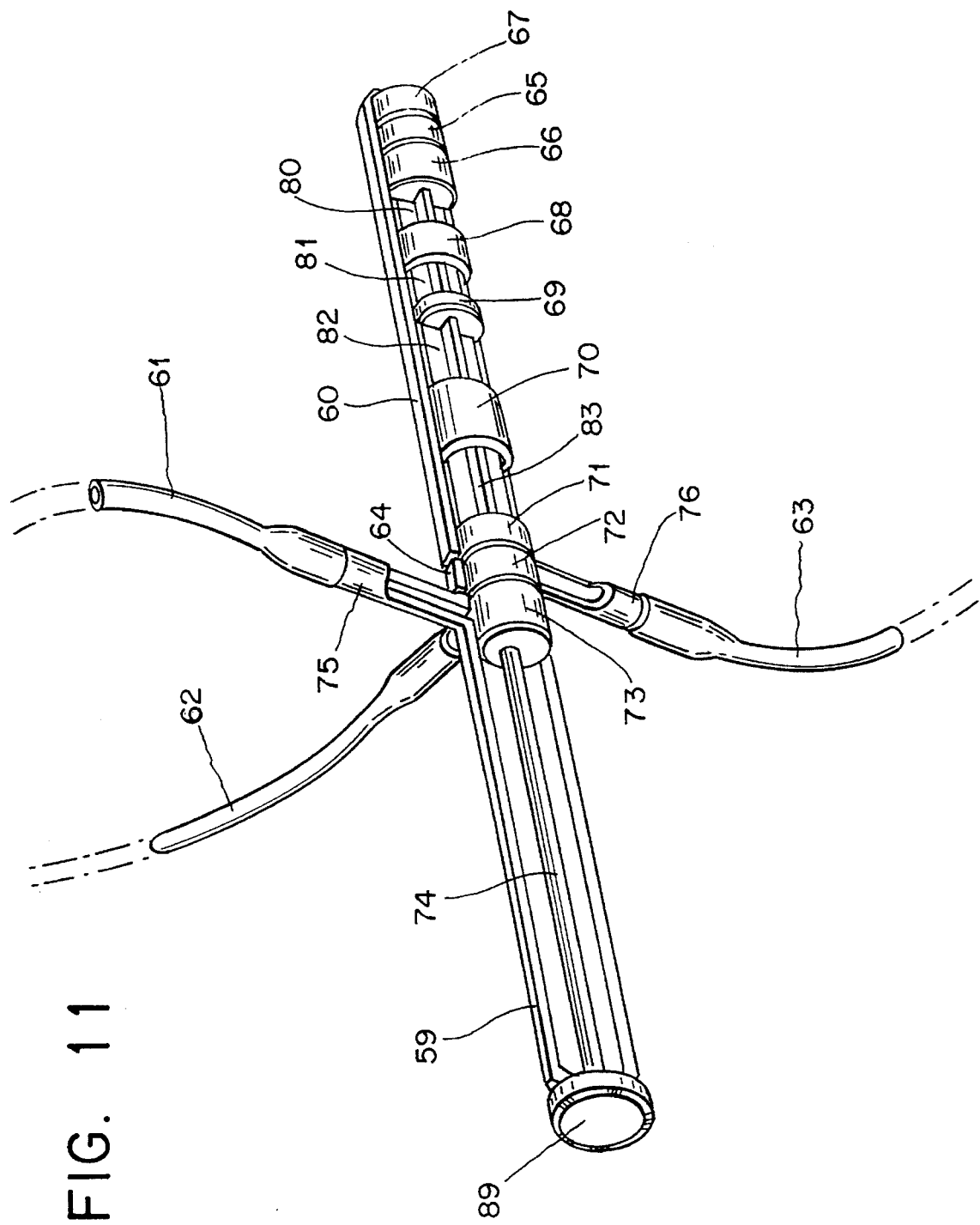

Finally, the fluid directing elements are pushed to the position shown in FIG. 11, in which the plugs 71, 72 and 73 seal the outlets to the "empty" fluid bag (now full of fluid drained from the catheter), the catheter and the "fresh" fluid bag (now empty) respectively. The catheter and its connecting means 64 may be removed from the device, completely sealed. The now full fluid bag, its connecting tubes 63 and 76, and component 60 containing the used fluid directing elements, are discarded. Component 59 and the now empty fluid bag connected to it may be used subsequently in the same way as component 60 and the original empty bag were used.

During use of the device of FIGS. 7–11, all fluid flow between the catheter and the two bags occurs via the intermediate conduit means represented by tubes 59, 60 and 64. Thus, fluid exchange takes place in a closed environment, free from risk of infection.

From the above description, it will be seen that one of the principal components of the devices shown in the figures is the catheter and its connecting means, the latter being in the form of a section of tube with the flexible catheter tube connected to its side wall in such a way as to allow fluid flow between the flexible tube and the inside of the connecting means. The resilient plug inside the connecting means ensures that the catheter is sealed at all times when the connecting means is in contact with the outside air. The construction of the connecting means makes it possible to mount similarly shaped connecting components to either side of it, in series, so that the plug inside the connecting means may be pushed into an adjacent component and/or a second sealing plug or other fluid directing element pushed from an adjacent component into the catheter connecting means. By means of such sequential movements of fluid directing elements through the inside of the connecting components (which together form an intermediate conduit means), it is possible to effect fluid exchanges within a sealed envelope.

The devices shown in the figures are by no means the only ways in which a device in accordance with the invention may be constructed. In particular, other shapes and arrangements of fluid directing elements (for instance, sealing plugs, spacers and the like), may be used to achieve a range of different flow patterns between two or more connected appliances. A simpler device might, for instance, not include fluid directing elements which allow the first stage of operation (ie, "flushing" of the system from a fresh fluid bag to an empty bag) to occur if not required.

Moreover, the support means for the device should not be limited to that shown in FIGS. 4 and 5. Many alternative arrangements are possible, as is a device which does not require support means at all. A device according to the invention may also be provided with support means which are specifically designed for use by patients having handicaps such as impaired sight or low manual dexterity.

FIGS. 12–20 illustrate a further device in accordance with the invention, which includes a support means generally labelled 99 in the form of a protective housing and drive means, in the housing, for moving fluid directing elements through the device. The device is again adapted for use in CAPD.

The operating mechanism of the previously described devices suffers from the drawback that the user needs to make a number of secondary operations in order to sequence the fluid directing elements through the required steps. Also, at the end of each sequence, the device has to be reset before its next use. The device of FIGS. 12–20 incorporates an alternative, and preferred, operating mechanism which dispenses with secondary operations and does not have to be reset after each use.

Figure 13:
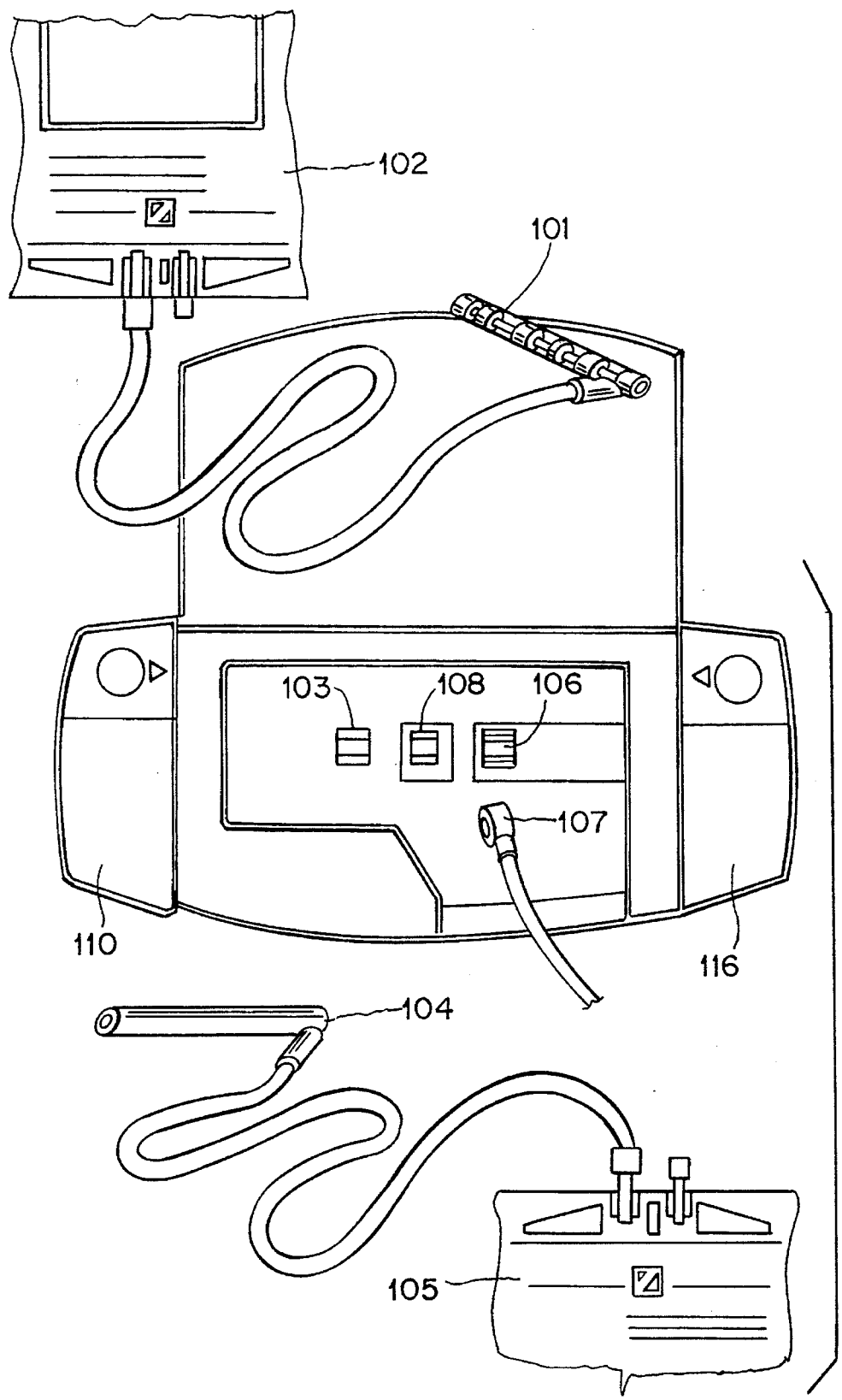
FIG. 13 shows a plan view of the support means of FIG. 12, together with medical appliances to be used with it.
Figure 14:
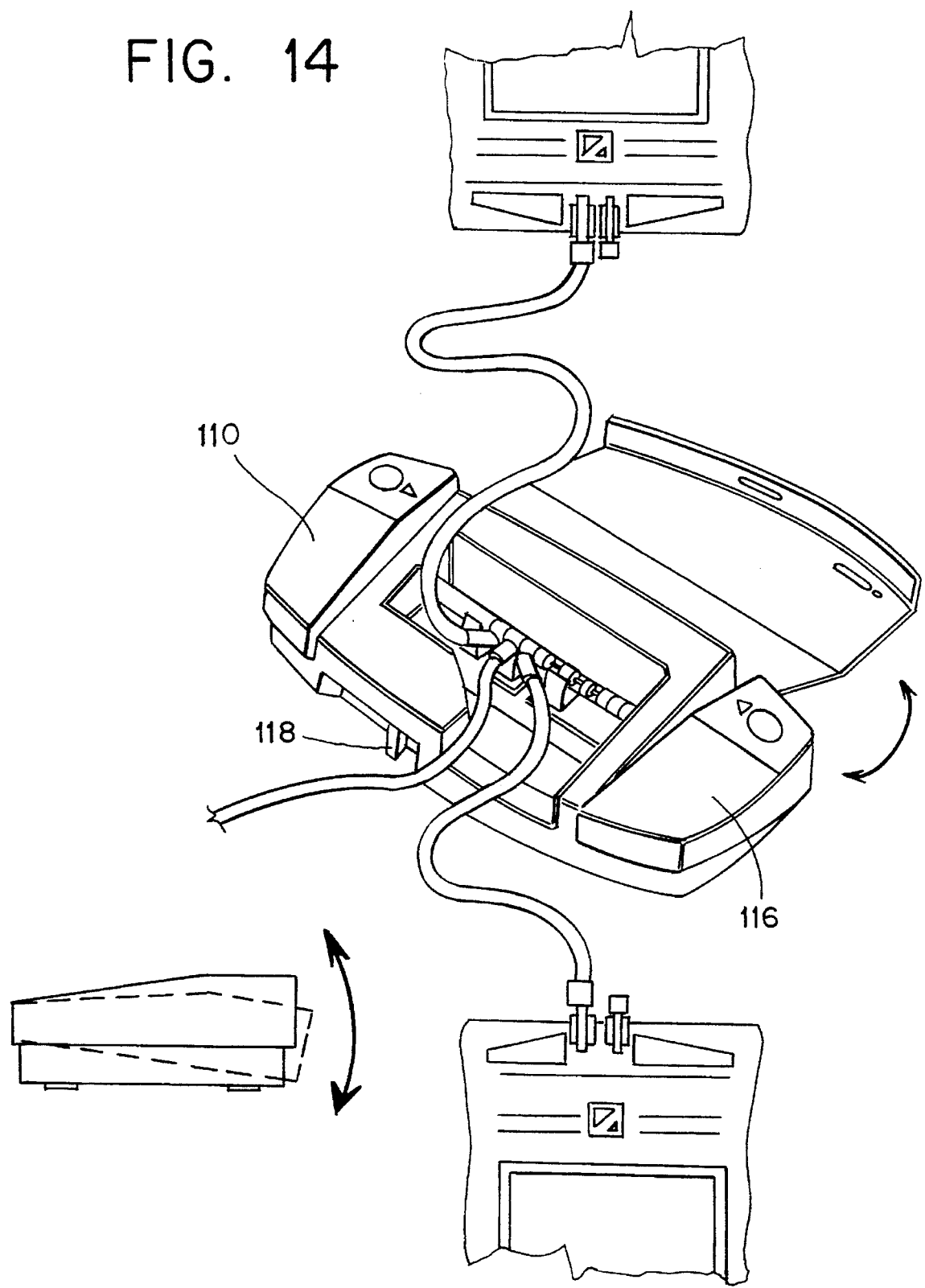
FIGS. 14 and 15 show in perspective view the complete device, including the support means of FIG. 12, in use.
Figure 15A:
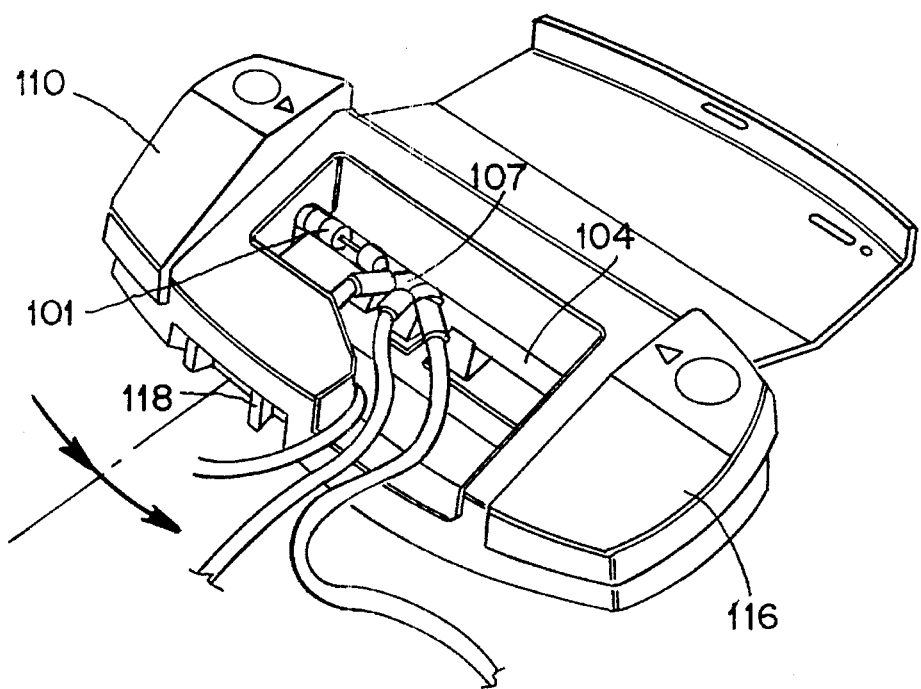
Figure 15B:
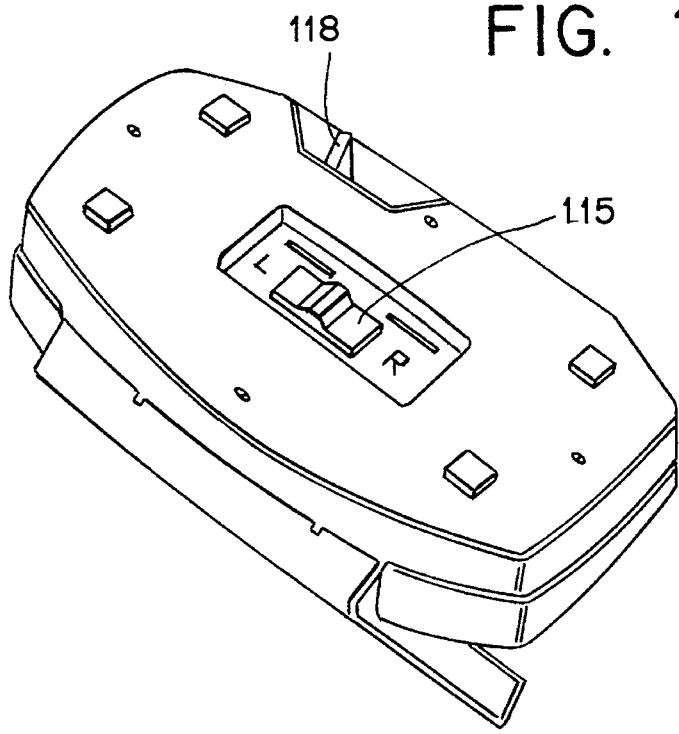

Referring firstly to FIG. 13, in use the connector 101 of a new fluid bag 102 is placed in a clip 103 in the support means of the device. The connector 104 of an empty fluid bag is clipped in a clip 106. The catheter connector 107 is placed in clip 108. The clamp lever 118 (see FIG. 15) is moved in the direction of the arrow to bring together the faces of the connectors 101, 104 and 107 in tight register.

To sequence the seal set (fluid directing elements) 109 (FIG. 17a) the lever 110 is depressed, causing spur gear 111 (FIG. 16) to rotate and drive the chain 113, which is made up of a series of connected "pushing pieces" such as 112 and 112a. Movement of the chain forward by one position (FIG. 17b) also pushes the seal set 109 forward by one position.

Figure 16:
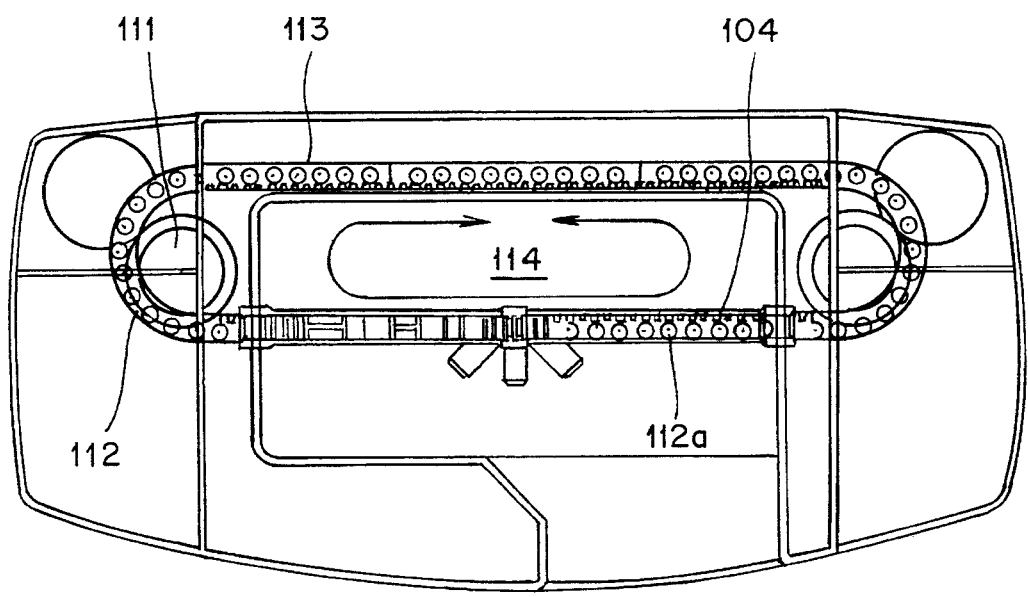
FIG. 16 is a transverse cross-section taken through the support means of FIG. 12.
Figure 17A:
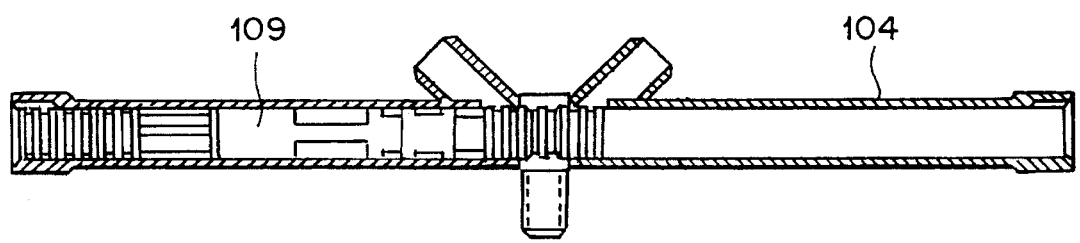
FIG. 17 is a transverse cross-section taken through the intermediate conduit means of the device of FIGS. 14 and 15, during various stages of use of the device.
Figure 17B:
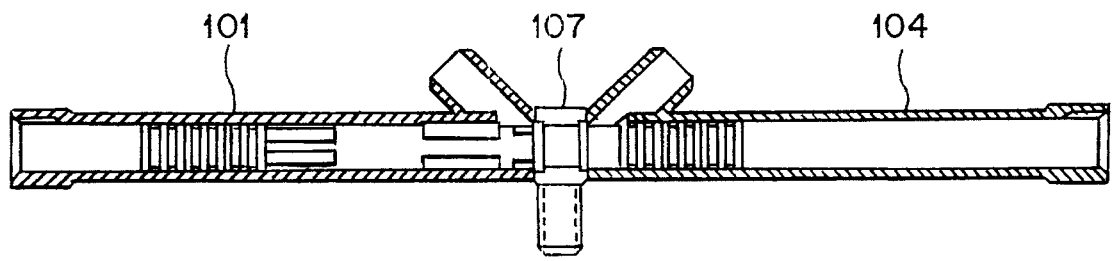
Figure 17C:
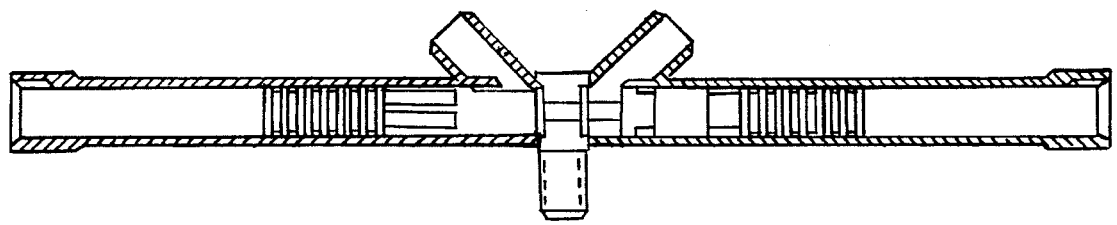
Figure 17D:
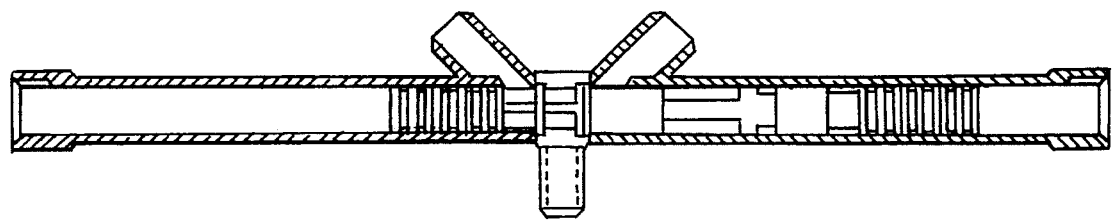
Figure 17E:
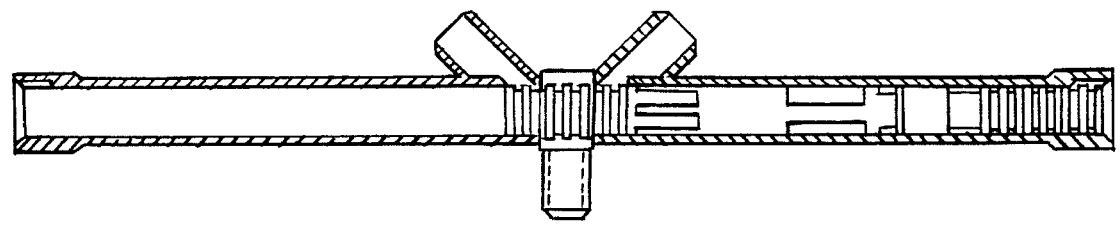
Figure 18:
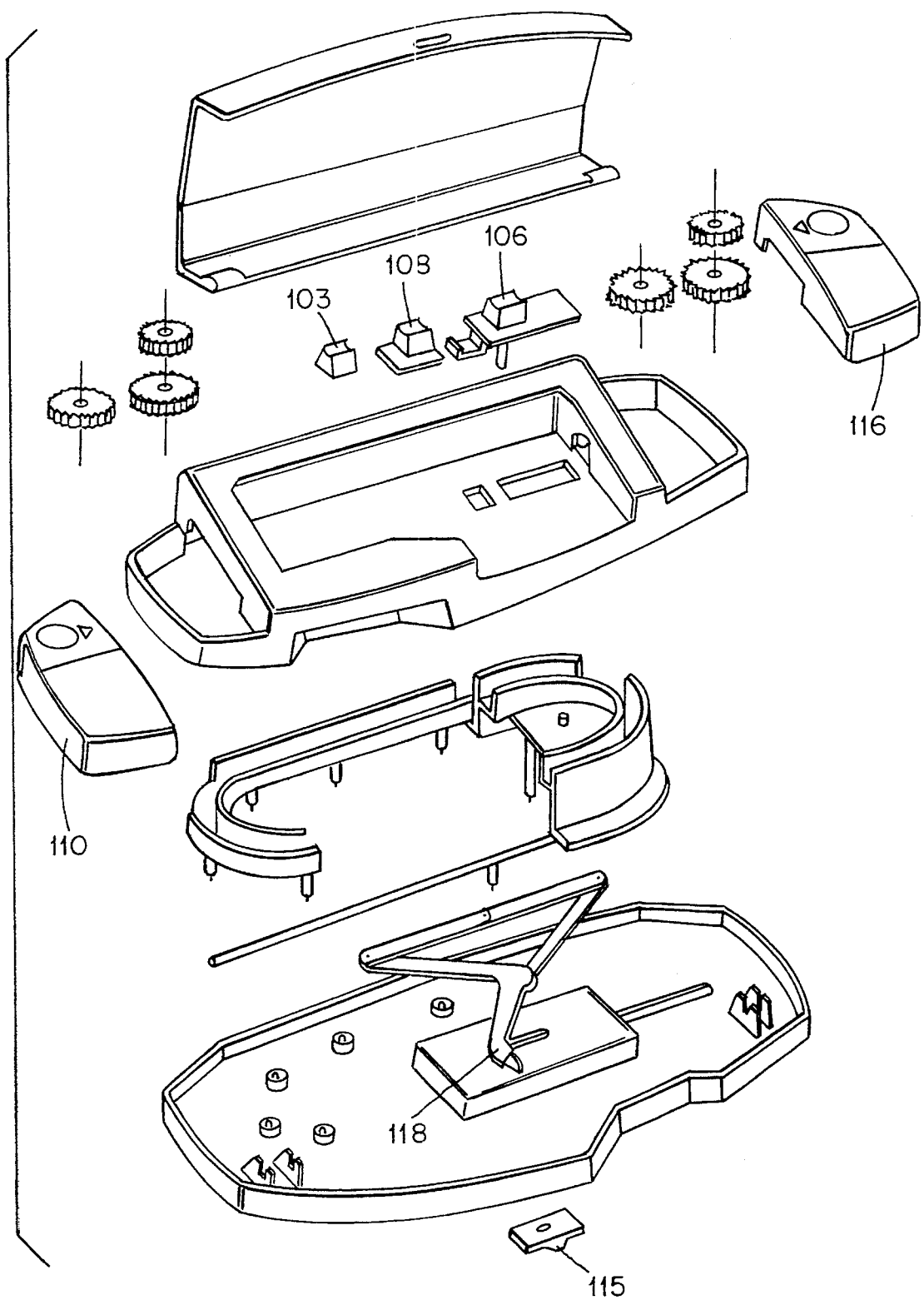
FIG. 18 is an exploded perspective view of component parts of the support means of FIG. 12.

This sequence is repeated four times to effect a complete bag exchange (FIGS. 17a–17e), during which the element labelled 112 in FIG. 16 is moved entirely into the full bag connector 101 and the element 112a entirely out of the empty bag connector 104. The full bag connector 101 now becomes an empty bag connector ready for the next fluid exchange. The device does not need to be reset in any way prior to re-use; the drive chain 113 is still suitably positioned to drive a fresh set of fluid directing elements through the device.

It will be understood that with connectors 101, 104 and 107 mounted and clamped in the support means 99 of the device, a continuous loop 114 (FIG. 16) is formed from the chain 113 and the seal set 109.

The description given is for operation where moving parts that make up the loop 114 move in an anti-clockwise direction, but in some circumstances it may be desirable to move the fluid directing elements in the opposite direction, in which case the operator of the device moves the interlock switch 115 (FIG. 15) from one position to the other which disengages the operating mechanism associated with lever 110 and engages the operating mechanism associated with lever 116. Operation of lever 116 causes the moving parts that make up the loop to move in a clockwise direction.

Figure 12A:
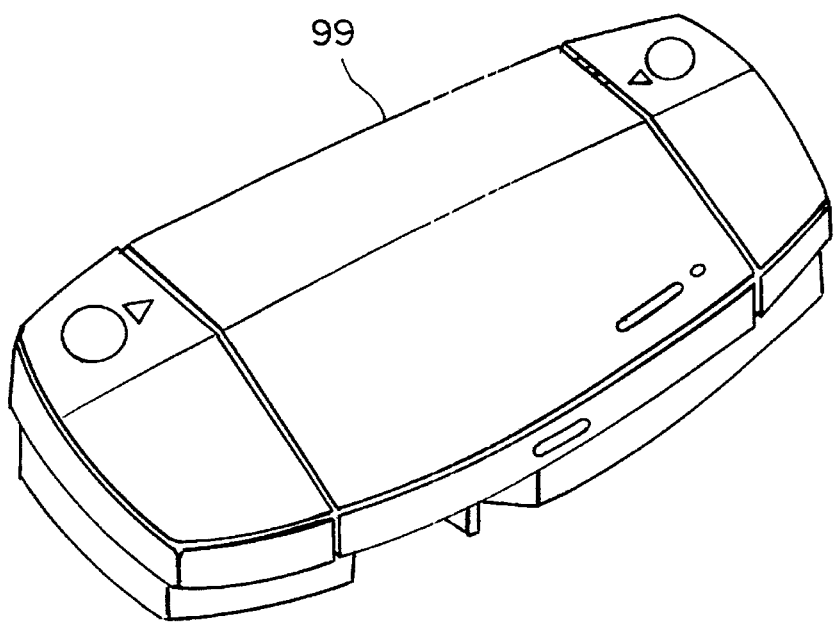
FIG. 12 shows in perspective view support means as part of a device in accordance with the invention, in both its closed and its open configuration.
Figure 12B:
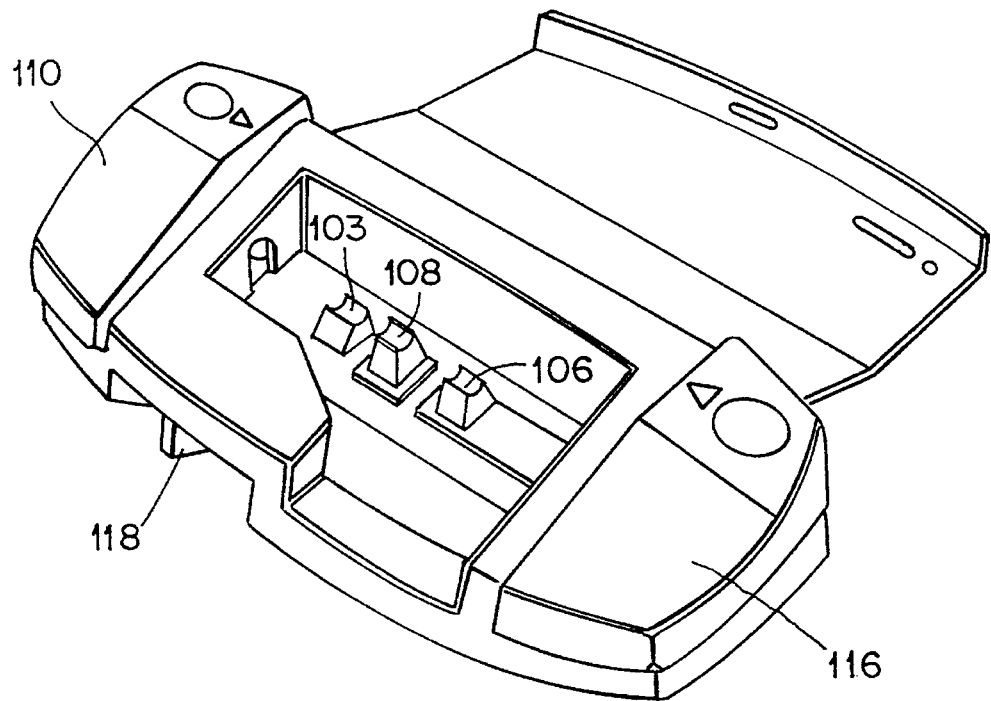
Figure 19:
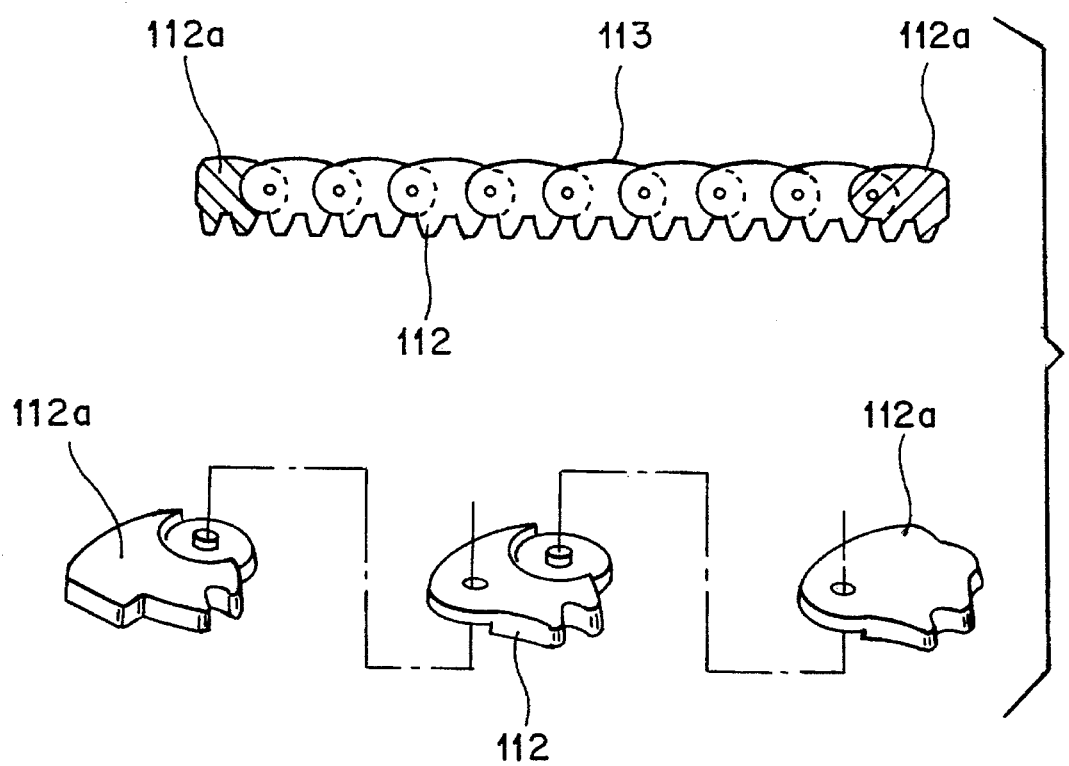
FIGS. 19 and 20 show parts of drive means incorporated in the support means.
Figure 20:
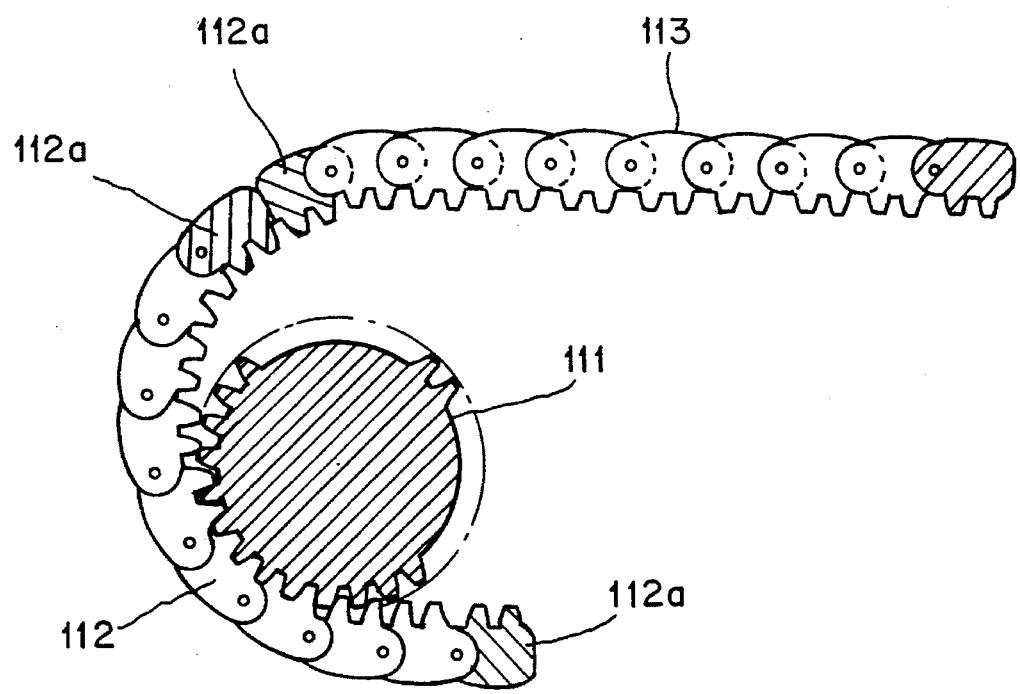

The housing 99 can be seen to include a protective cover, shown closed in FIG. 12a and open in FIG. 12b. It also incorporates the chain 113 of hingedly connected pushing elements such as 112 and 112a, driven by gear 111 through the intermediate conduit means formed by connectors 101, 104 and 107. FIG. 19 shows in more detail component parts of the chain 113, and FIG. 20 the way that they engage with gear 111 in use. The chain is made up of "sets" of pushing pieces, each of which comprises two end components 112a and eight connected middle components 112. The end components of each set are separable from those of adjacent sets, allowing connectors 101, 104 and 107 to be removed and replaced as described above after each fluid exchange, without the need to reset the chain.

I claim:

1. A connecting device for use in connecting together open ends of two or more medical instruments so as to control a flow of fluid between the medical instruments, said connecting device comprising:

intermediate conduit means having two or more ports to which open ends of the two or more medical instruments are connectable; and, a plurality of fluid directing members located inside said intermediate conduit means and movable linearly therein in an end-to-end abutting relationship, so that each of said fluid directing members has a first end and a second end and are arranged along said intermediate conduit means so that said first end and said second end, respectively, of adjacent said fluid directing members abut one another, said fluid directing members being operable for allowing, or restricting, the flow of fluid, via said intermediate conduit means, between two medical instruments when the medical instruments are connected to the ports of said intermediate conduit means, depending upon a linear position of said fluid directing members inside said intermediate conduit means, said fluid directing members being movable within said intermediate conduit means from a first position, wherein said fluid directing members act to close all the ports in said intermediate conduit means to fluid flow, to a second position, wherein said fluid directing members allow fluid flow between two of said medical instruments connected to said connecting device, to a third position, wherein all the ports of said intermediate conduit means are closed to fluid flow between said intermediate conduit means and said two medical instruments, the movement of said fluid directing members being a sequential movement, in one direction, from each position to the next.

2. The connecting device according to claim 1, wherein said intermediate conduit means includes a cylindrical tube.

3. The connecting device according to claim 1, further comprising biassing members for biassing said fluid directing members into a position wherein said fluid directing means obstruct the fluid flow into, or out of, one of said medical instruments connected to said connecting means, but are movable out of said position, against the bias of said biassing means, for permitting a desired fluid flow.

4. The connecting device according to claim 1, wherein said fluid directing members include one or more sealing members for a sealing engagement with said intermediate conduit means for closing one or more of the ports to the fluid flow.

5. The connecting device according to claim 4, wherein each of said sealing members provides a continuous peripheral seal with said intermediate conduit means.

6. The connecting device according to claim 4, wherein said sealing members are plugs made of a resilient material, said plugs being capable of a sliding movement along the inside of said intermediate conduit means.

7. The connecting device according to claim 4, wherein said fluid directing members include one or more shaped members, which are shaped for allowing fluid flow between two of the ports of said intermediate conduit means when said fluid directing members are appropriately positioned in said intermediate conduit means.

8. The connecting device according to claim 7, wherein said fluid directing means, which allow fluid flow between the ports of said intermediate conduit means, are spacers which maintain an appropriate spacing between other of said fluid directing members, said spacers being shaped for allowing the fluid flow around the spacers between two ore more ports of said intermediate conduit means.

9. The connecting device according to claim 1, further comprising drive means for moving, or for assisting movement of, said fluid directing members within said intermediate conduit means.

10. The connecting device according to claim 9, wherein said drive means comprises a plunger operable from outside one end of said intermediate conduit means, said plunger being able to be depressed for pushing said fluid directing members through said intermediate conduit means.

11. The connecting device according to claim 1, further comprising first connecting means and second connecting means, each adaptable for sealing open ends of said medical instruments, said first connecting means and said second connecting means each including respective lengths of conduit adapted for placement end-to-end adjacent one another for forming said intermediate conduit means, said first connecting means and said second connecting means each including fluid directing members which on placement of said connecting adjacent one another to form said intermediate conduit means are located inside said intermediate conduit means, said connecting device thereby being in a modular form.

12. The connecting device according to claim 11, wherein said fluid directing members, on placement of said connecting means adjacent one another for forming said intermediate conduit means, are located in a first limiting position at which said fluid directing members seal said medical instruments from said intermediate conduit means, said fluid directing members being movable through an intermediate position at which said fluid directing members allow fluid flow through said intermediate conduit means between said medical instruments to a second limiting position, at which said fluid directing members seal said medical instruments from said intermediate conduit means, said first connecting means and said second connecting means being separable when said fluid directing members are in their second limiting position, wherein in said second limiting position each of said connecting means includes one or more of said fluid directing members which seal the open end of a respective said medical instrument.

13. The connecting device according to claim 1, wherein said fluid directing members are movable linearly within said intermediate conduit means from a first limiting position, at which said fluid directing members are able to seal three medical instruments from said intermediate conduit means, through two intermediate positions, in which said fluid directing members seal a respective one of said medical instruments from said intermediate conduit means, for allowing fluid flow through said intermediate conduit means between the remaining two of said medical instruments, to a second limiting position, wherein said fluid directing members seal all three of said medical instruments from said intermediate conduit means.

14. The connecting device according to claim 13, comprising first connecting means, second connecting means and third connecting means, each adapted for sealing the open ends of the medical instruments and for placement adjacent one another for forming said intermediate conduit means, said first, second and third connecting means including said fluid directing members, which on placement of said connecting means adjacent one another for forming said intermediate conduit means, are located inside said intermediate conduit means in a first limiting position, at which said fluid directing members seal all three of said medical instruments from said intermediate conduit means, said fluid directing members being movable through two intermediate positions wherein said fluid directing members seal a respective one of said medical instruments from said intermediate conduit means, for allowing fluid flow through said intermediate conduit means between the remaining two of said medical instruments, to a second limiting position at which said fluid directing members seal all three of said medical instruments from said intermediate conduit means being separable from one another when said fluid directing members are in their second limiting position, wherein in said second limiting position, each of said connecting means includes at least one of said fluid directing members which seal the open end of one of said medical instruments.

15. The connecting device according to claim 1, for use during fluid exchange in continuous ambulatory peritoneal dialysis in connecting together and controlling fluid flow between (a) a catheter having an inlet, (b) a receiver bag having an inlet for receiving fluid drained from a body via the catheter, and (c) a fresh fluid bag having an outlet and containing fresh fluid For infusion into the body via the catheter, said connecting device including a first of said fluid directing members which, when positioned adjacent the outlet of the fresh fluid bag and the inlet of the receiver bag, allows fluid flow from the fresh fluid bag to the receiver bag, but not into, or out of, the catheter; a second of said fluid directing members when, when positioned adjacent the inlet of the catheter and the inlet of the receiver bag, allows fluid flow from the catheter to the receiver bag, but not into, or out of, the fresh fluid bag; a third of said fluid directing members which, when positioned adjacent the outlet of the fresh fluid bag and the inlet of the catheter, allows fluid flow from the fresh fluid bag to the catheter, but not into, or out of, the receiver bag; and, a fourth of said fluid directing members which, when positioned in said intermediate conduit means across the inlet of the catheter and the outlet of the fresh fluid bag and the inlet of the receiver bag acts to prevent fluid flow between said intermediate conduit means and any of said medical instruments.

* * * * *